United States Patent [19]

Anzai et al.

[11] Patent Number: 4,875,484

[45] Date of Patent: Oct. 24, 1989

[54] METHOD FOR GENERATING A LOW FREQUENCY ELECTRIC STIMULUS SIGNAL AND LOW FREQUENCY ELECTRIC STIMULUS SIGNAL GENERATING APPARATUS

[75] Inventors: Hiroshi Anzai; Atsunori Futsuki, both of Tokyo, Japan

[73] Assignee: Total Human Medical Laboratory Co., Ltd., Tokyo, Japan

[21] Appl. No.: 103,010

[22] Filed: Sep. 30, 1987

[30] Foreign Application Priority Data

| Oct. 4, 1986 | [JP] | Japan | 61-236700 |
| Oct. 8, 1986 | [JP] | Japan | 61-239632 |
| Oct. 8, 1986 | [JP] | Japan | 61-239633 |
| Oct. 8, 1986 | [JP] | Japan | 61-239634 |
| Oct. 8, 1986 | [JP] | Japan | 61-239635 |
| Oct. 8, 1986 | [JP] | Japan | 61-239637 |
| Oct. 8, 1986 | [JP] | Japan | 61-239638 |

[51] Int. Cl.⁴ ............................................. A61N 1/36
[52] U.S. Cl. .................................... 128/421; 128/422
[58] Field of Search .................. 364/413, 417, 487; 128/421, 422, 420.5

[56] References Cited

U.S. PATENT DOCUMENTS

| 2,810,453 | 1/1958 | Mayne . | |
| 3,449,768 | 6/1969 | Doyle . | |
| 3,490,458 | 1/1970 | Allison . | |
| 4,338,945 | 7/1982 | Kosugi et al. | 128/421 |
| 4,390,023 | 6/1983 | Rise | 128/421 |
| 4,431,000 | 2/1984 | Butler . | |
| 4,453,548 | 6/1984 | Maurer | 128/421 |
| 4,503,863 | 3/1985 | Katims | 128/421 |
| 4,541,432 | 9/1985 | Molina-Negro et al. | 128/421 |
| 4,598,713 | 7/1986 | Hansjurgen et al. | 128/421 |
| 4,664,117 | 5/1987 | Beck . | |
| 4,688,574 | 8/1987 | Dufresne et al. | 128/421 |

FOREIGN PATENT DOCUMENTS

| 204525 | 10/1986 | European Pat. Off. . |
| 3207050 | 9/1983 | Fed. Rep. of Germany . |
| 5543 | 2/1981 | Japan . |
| 22921 | 5/1981 | Japan . |
| 30062 | 10/1983 | Japan . |
| 44061 | 3/1984 | Japan . |
| 8602567 | 10/1984 | PCT Int'l Appl. . |

*Primary Examiner*—Leo P. Picard
*Attorney, Agent, or Firm*—Pollock, VandeSande & Priddy

[57] ABSTRACT

A method for generating a low frequency electric stimulus signal is carried out by generating electric stimulus signal to provide electric stimulus to a biological body or living body. Either the current or voltage, or both, can be controlled in accordance with sound volume levels supplied from a sound source to modulate the electric stimulus signal. The frequency of the electric stimulus signal is selected to be a low frequency.

A low frequency electric stimulus signal generating apparatus for applying electric stimulus to a biological body includes a control section and a current/voltage controlling section. In the control section, a sound volume level derived from a sound source is sampled at a rate at which the biological body can feel it in substantially real time. The respective sampled sound levels are converted into frequencies corresponding to low frequencies and output, and predetermined control information. In the current/voltage controlling section, current and voltage stimulus signals are frequency-modulated separately based upon the frequencies. The control section and current/voltage controlling section are included in a stimulus signal generating section.

66 Claims, 14 Drawing Sheets

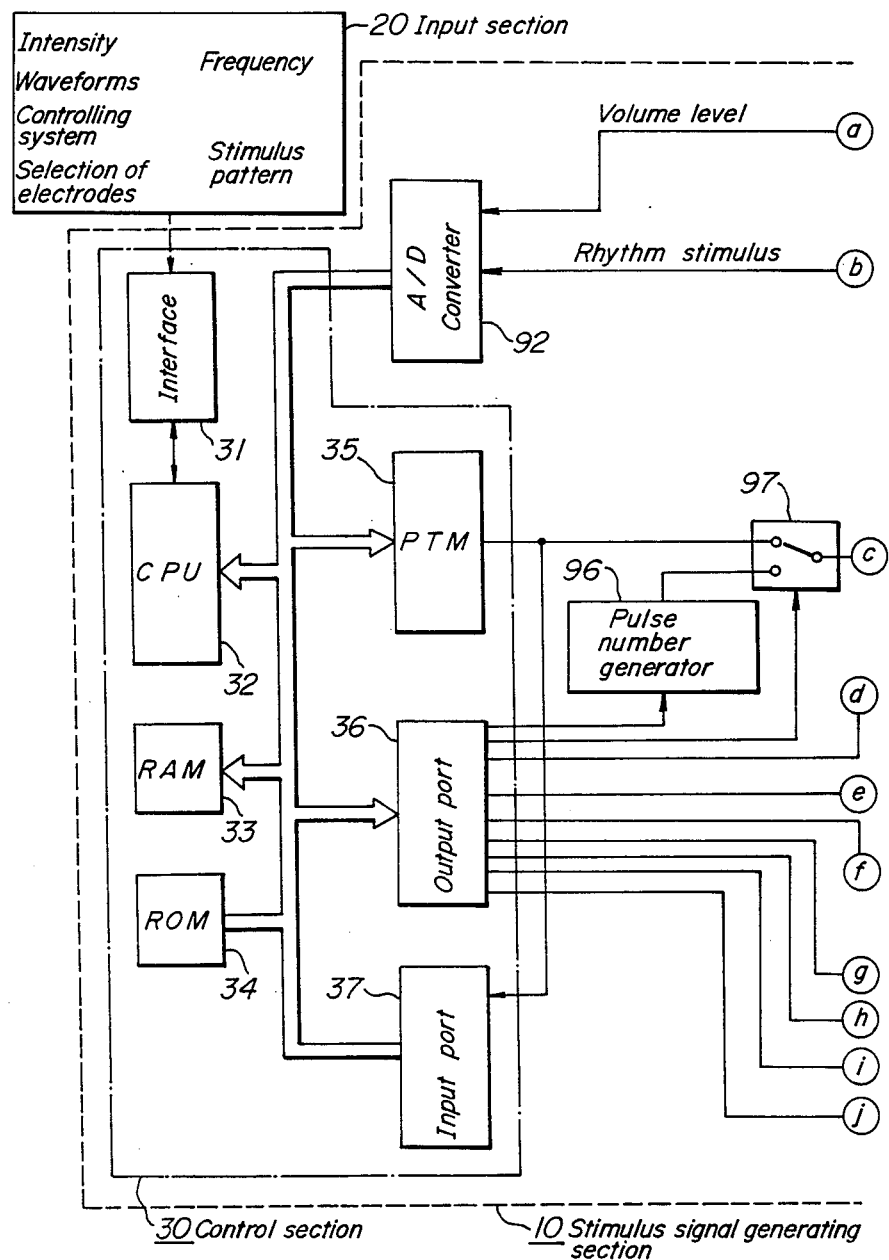
FIG_2A

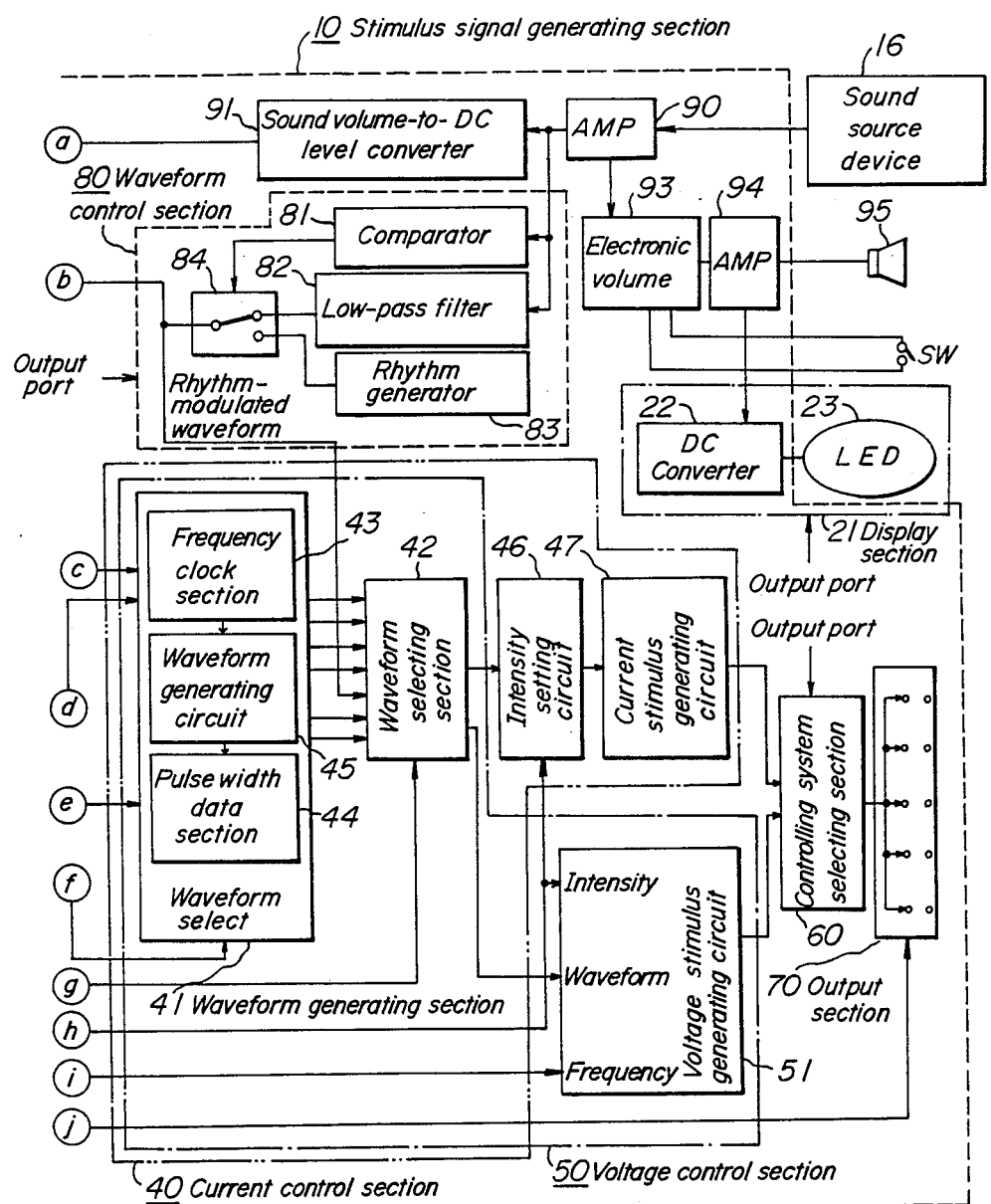
FIG_2B

FIG_3A 
FIG_3B 
FIG_3C 
FIG_3D 
FIG_3E 
FIG_3F 
FIG_3G 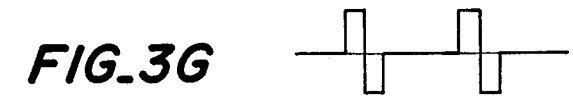
FIG_3H 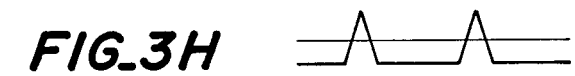
FIG_3I 
FIG_3J 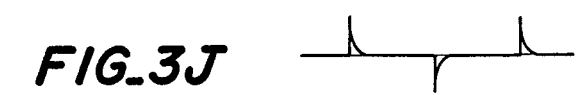
FIG_3K 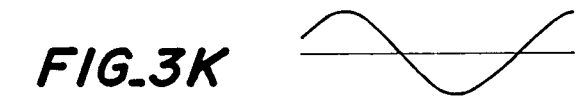

FIG. 4

Table conversion

| Step | 0 | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|---|
| Hz | 1.5 | 2 | 2.5 | 3 | 4 | 5 | 6 | 7 | 8 | 9 | 10 | 15 | 17 | 22 | 27 | 30 |

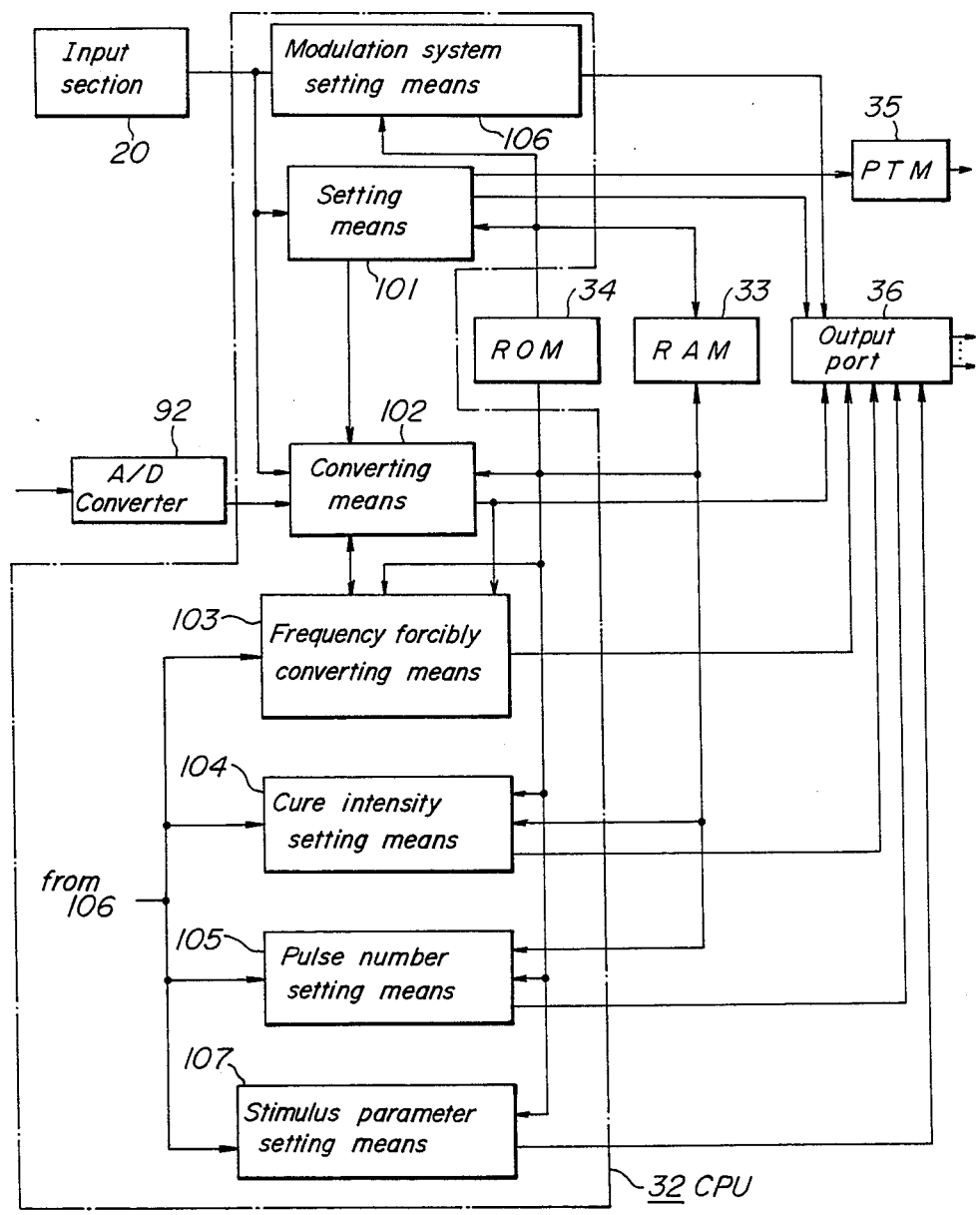
FIG_5

FIG_6
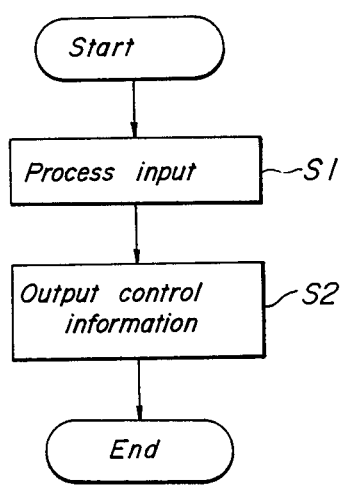
FIG_7
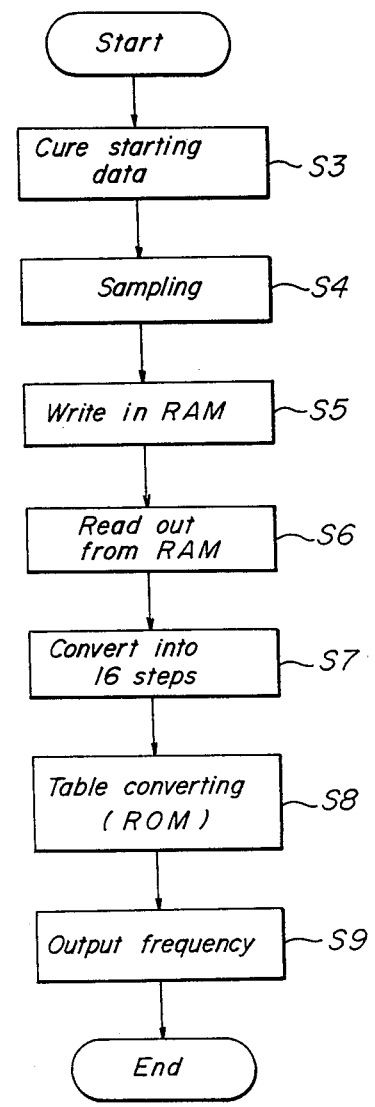

FIG_8
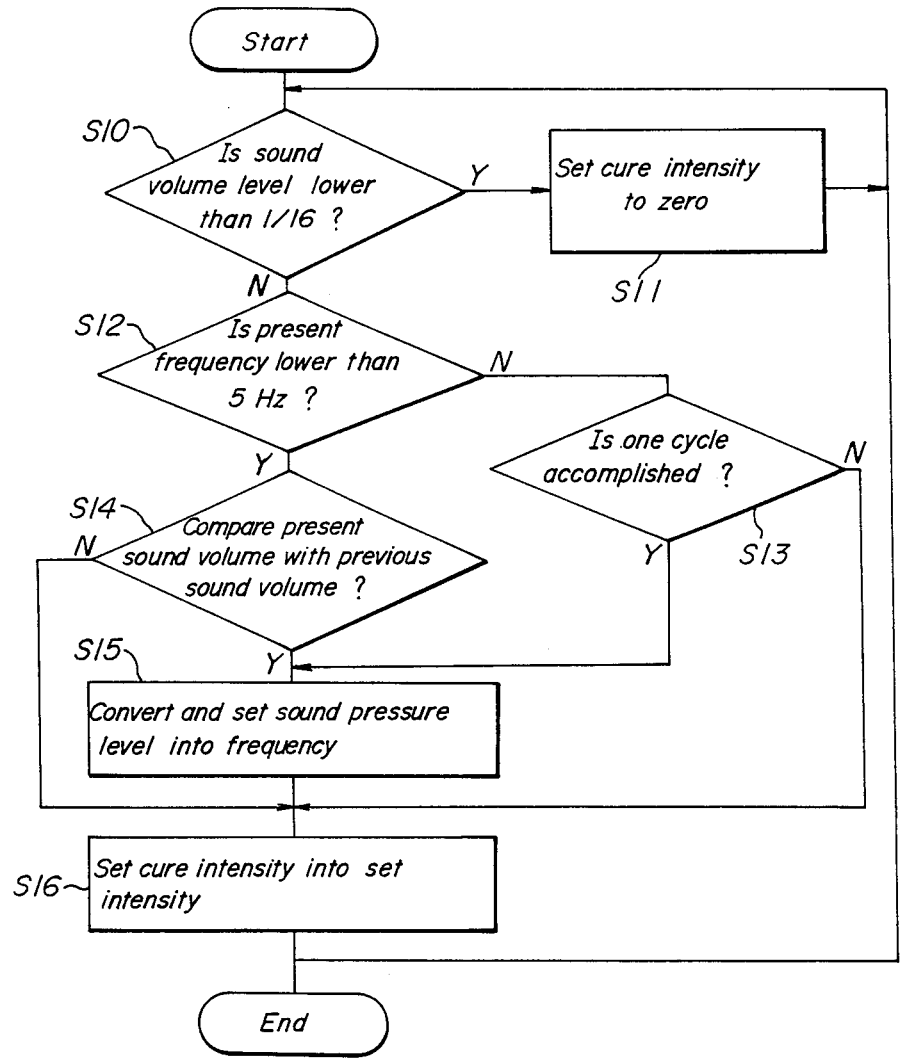

FIG_9
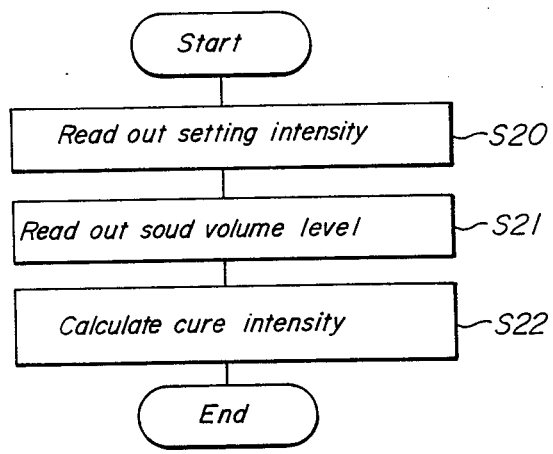
FIG_10
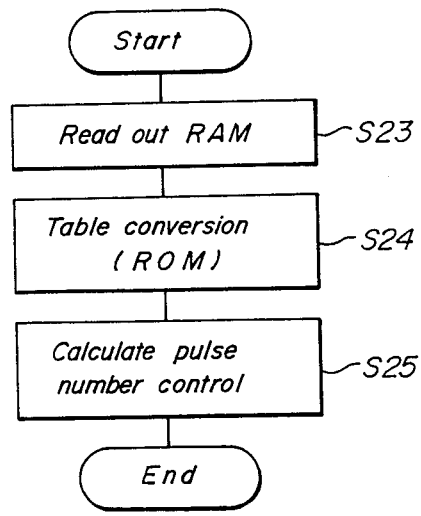

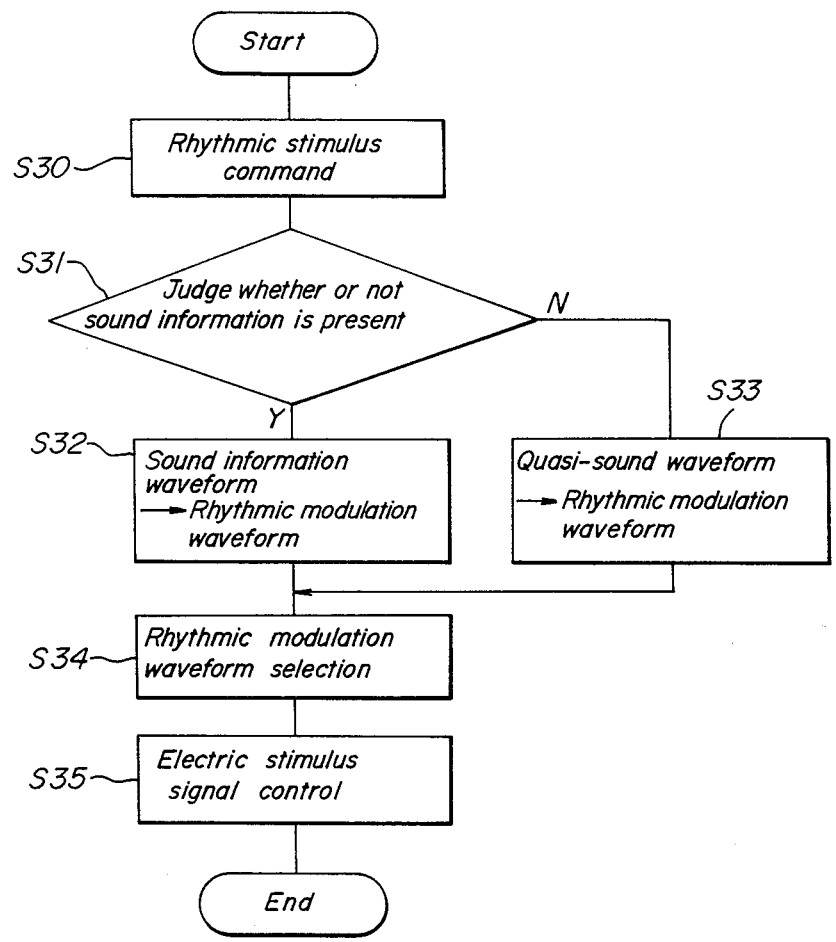
FIG_11

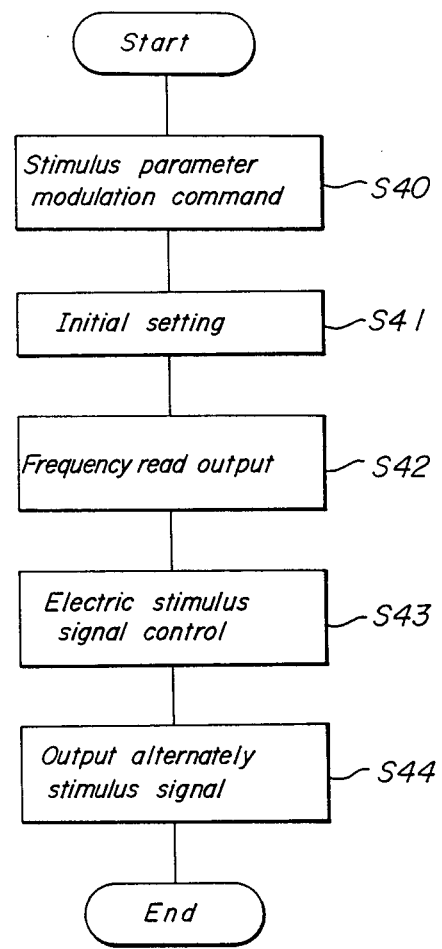
FIG_12

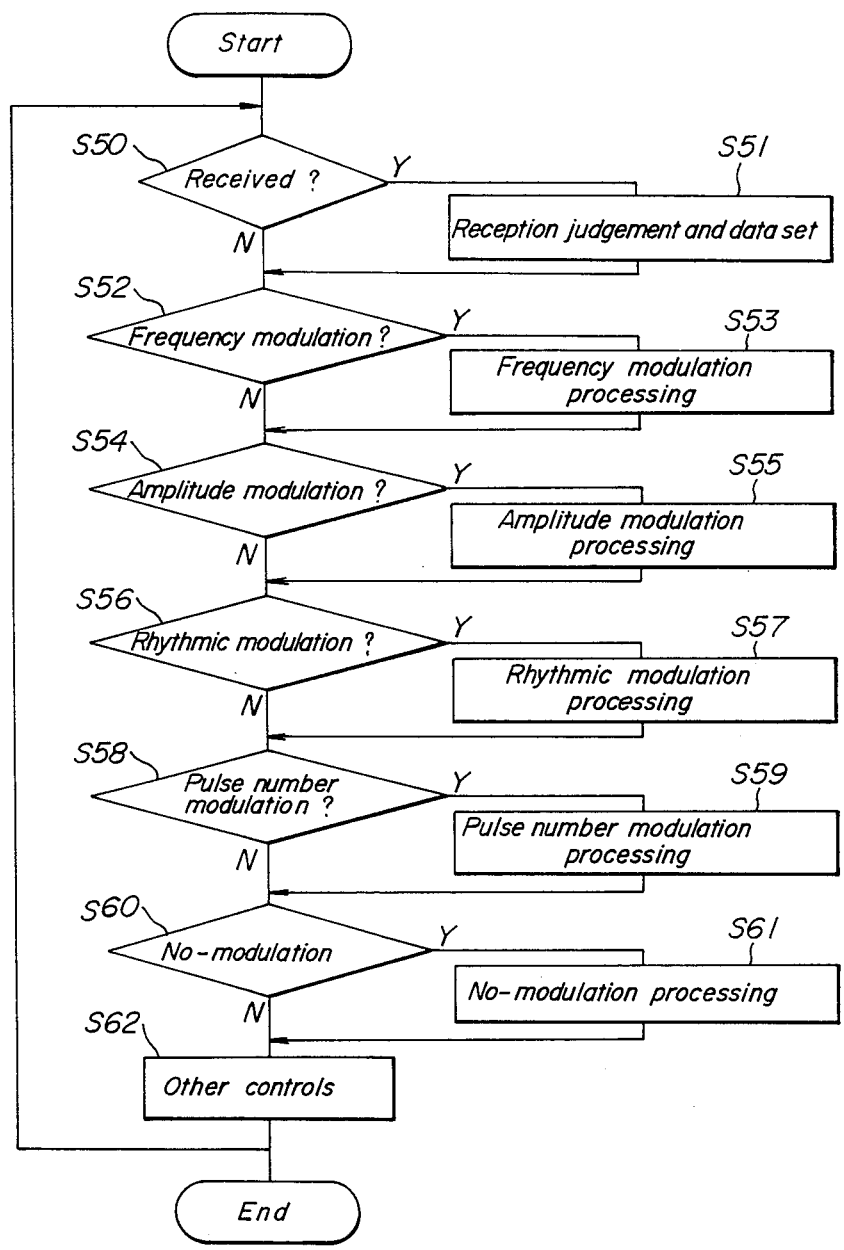
FIG_13

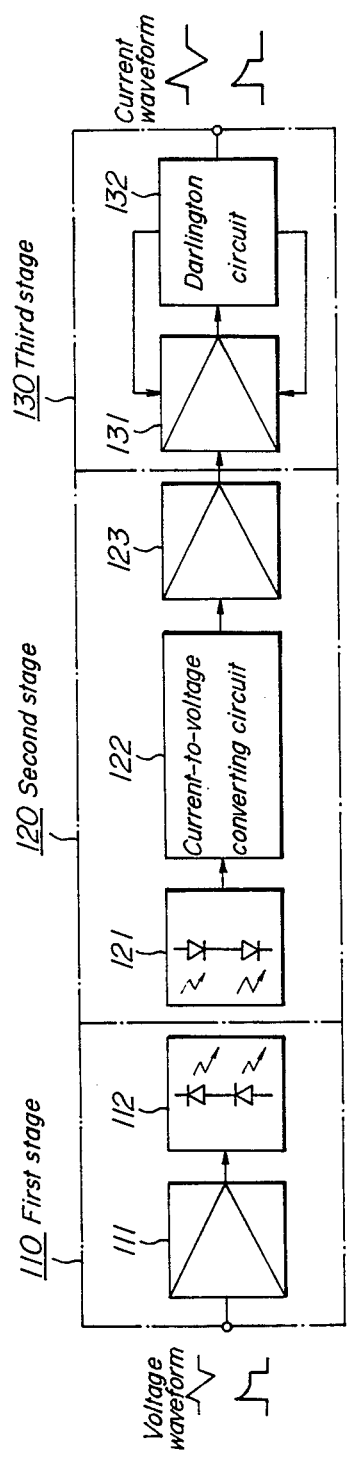
FIG._15
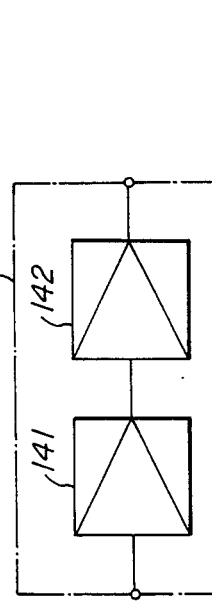
FIG._16

METHOD FOR GENERATING A LOW FREQUENCY ELECTRIC STIMULUS SIGNAL AND LOW FREQUENCY ELECTRIC STIMULUS SIGNAL GENERATING APPARATUS

BACKGROUND OF THE INVENTION

1. Field of the Invention

The present invention relates to a method of generating a low frequency electrical stimulus signal to provide an electrical stimulus to a biological body, and also to an apparatus for generating a low frequency electrical stimulus signal.

2. Description of Prior Art

It is known that when audible, or hearing stimulus is provided to a biological body by, for instance, playing classical music, curative effects for pain, shoulder discomfort, unpleasant feeling and so on can be achieved since the pleasantness or unpleasantness felt by the biological body is based upon the experimental conception, or the body's concentration is directed to other matters than pain and unpleasant feelings. Similarly, it is also known that when electric stimulus (skin, or percutaneous stimulus) is given to a biological body, the pain, shoulder discomfort and other unpleasant feelings can be relaxed, or cured.

According to experimental studies, it is also known that a biological body can feel more refresh stimulus, which can achieve higher curative effects, under the condition that a stimulus given at a higher rate per unit of time to the biological body is better than a stimulus which is given to the body at a lower rate per unit of time, and the stimulus regularly given is better than the stimulus irregularly given.

Based upon the above-described facts, various curative methods have been developed to reduce pain by utilizing the above stimulus.

For a conventional electric stimulus signal generating technique, there has been proposed, for instance, a method of producing an electric stimulus signal, the pulse repetition frequency of which is not varied in accordance with a lapse of time, and giving such a stimulus signal to a biological body, especially to the body's sympathetic nerves and parasympathetic nerves. Moreover, a conventional electric stimulus signal generating apparatus is known from, for example, Japanese patent publication No. 56-5543 (referred to as a "printed publication I") and Japanese utility model publication No. 56-22921 (referred to as a "printed publication II").

The first reference describes such a technique in accordance with the 1/f fluctuation theory, i.e., the signal of music being analyzed in the frequency spectrum, and the power spectrum density of the analyzed signal being inversely proportional to the frequency, while the frequency of the electric stimulus signal is changed in a relatively long time range from 0.5 to 4 seconds within a range from 10 to 100 Hz, for producing the electric stimulus signal.

On the other hand, the second reference describes a technique of recording the pulse repetition frequency of the electric stimulus signal and also the irregular pulse pattern when the generating duration time of the same pulse repetition is varied, and reproducing the recorded data from the recording medium in accordance with the 1/f fluctuation theory.

Since, as is known in this field, the tempo of music is synchronized with the nerve and furthermore tissue and cells, the effects to reduce pain can be emphasized. Accordingly, this effect can be realized in that if the sound volume level (i.e., sound pressure level) is used as the sound information, the percutaneous stimulus can be provided to a biological body in synchronism with the tempo of the music.

However, since according to the above-described conventional technique, the percutaneous stimulus is provided to a biological body in accordance with the frequency of the 1/f fluctuation theory, it is practically difficult to adjust this stimulus with the tempo of the music.

Moreover, it is known in this field that when the audible, or hearing stimulus such as music and sounds, and the percutaneous stimulus (electric stimulus) reflecting the sound information are combined and provided to a biological body, a greater curative effect to reduce the mental pain can be expected as compared with a single stimulus. The curative effect may be further emphasized when both the hearing stimulus and the electric stimulus are given to a biological body in substantially real time.

However, according to the conventional techniques, neither method can provide both stimulus to a biological body in real time. Accordingly, since the electric stimulus is given to a biological body even when the music is under rest condition (in case of rest mode and lower sound pressure), this stimulus is not matched with the experimental mental reduction of unpleasantness of a biological body. As a result, the biological body feels this stimulus as the continuous variation of mere stimulus patterns, so that there is not as much curative effect to reduce the pain.

SUMMARY OF THE INVENTION

Primary objects of the present inventions are to provide methods and apparatus for generating a low frequency electric stimulus signal which can provide the electric stimulus signal (percutaneous stimulus) to a biological body in synchronism with the tempo of the hearing stimulus.

Secondary objects of the present inventions are to provide methods and apparatus for generating a low frequency electric stimulus signal, wherein the hearing stimulus can be given to a biological body in synchronism with the percutaneous stimulus in substantially real time.

To attain these objects of the present invention, according to the low frequency electric stimulus signal generating method of the invention, either one or both of the current or the voltage is controlled in response to the sound volume level supplied from the sound source to modulate the electric stimulus signal. It should be noted that the frequency of the electric stimulus signal employed in the present invention is selected to be a low frequency.

For the first embodiment, the sound volume level is first sampled at the rate at which a biological body feels it in substantially real time; secondly, the respective sound levels obtained by the sampling are converted into frequencies corresponding to the low frequency region; and thirdly, current or voltage frequency modulation is performed by these frequencies to control either the current or voltage.

In this embodiment, the low frequency range of the sound volume level-to-frequency conversion is preferably selected to be from 0 to 60 Hz.

Moreover, according to the first embodiment, the sound volume level is first sampled at a predetermined rate at which a biological body feels it in substantially real time; secondly, the respective sound volume levels acquired by this sampling operation are converted into amplitude control values corresponding thereto; and finally, the amplitude modulation is carried out in accordance with these amplitude control values within a range of 0 to 100% of the initially set amplitude value of the voltage or current, so as to control the current or voltage.

In addition, according to the first embodiment, the sound volume level is sampled at a predetermined rate at which a biological body feels it at substantially real time; secondly, the respective sound levels obtained by this sampling operation are converted into the pulse number control values; and thirdly, the pulse number modulation is carried out in accordance with these pulse number control values so as to effect the current or voltage control.

In the preferred embodiment, the pulse number modulation is performed in such a manner that the number of the pulse is equal to from 0 to 30 in response to the second volume level. Moreover, the above-described sampling operation is performed in a period from 0.01 to 0.5 second.

According to the low frequency electric stimulus signal generating apparatus of a second embodiment of the invention, a control section wherein a sound volume level derived from a sound source is sampled at a rate at which the biological body can feel it in substantially real time is concluded, the respective sample sound levels are converted into frequencies corresponding to low frequencies and output, and predetermined control information, and a current/voltage controlling section where current and voltage stimulus signals are frequency-modulated separately based upon the frequencies, the control section and current/voltage controlling section are included in a stimulus signal generating section.

For the second embodiment of the invention, the stimulus generating section includes a control system selecting section for switching only one of the current and voltage stimulus signals based upon control information derived from the control section and for outputting the same as the electric stimulus signal.

Moreover, according to the second embodiment, the current control section includes a waveform generating section for outputting a voltage waveform signal corresponding to the sound volume levels, and a current stimulus signal generating circuit for outputting a current stimulus signal having the same waveform as that of an input voltage waveform signal.

In addition, according to the second embodiment, the control section includes a waveform generating section for generating a voltage waveform signal having a frequency corresponding to the sound volume level, and a voltage stimulus signal generating circuit for outputting the input voltage waveform signal as a voltage stimulus signal.

Furthermore, according to the second embodiment, the low frequency region is preferably determined by 0 to 60 Hz.

Moreover, according to the second invention, the sampling period is preferably selected to be 0.01 to 0.5 second.

In the preferred embodiment, the control section includes means for subdividing the sound volume levels into a plurality of level steps, ROM for previously storing a sound volume level-to-frequency conversion table, and means for reading out from the ROM a frequency corresponding to the sound volume level at each sampling operation.

In the preferred embodiment, the sound volume level is set to a zero level of the sound volume level when the sound volume level is equal to a zero level, or a lower level.

In accordance with the first and second embodiments, controlling of the current or voltage is performed based upon the sound pressure level of the sound information to irregularly modulate the electric stimulus signal. Accordingly, a biological body can be stimulated by electric stimulus in response to the tempo of the sound information. Also, no stimulus time period can be made with the hearing stimulus when the music is at rest, or the sound volume level is low. As a result, percutaneous stimulus is provided to the biological body at the timing at which the biological body feels in substantially real time, and thus the curative effects of the musical cure according to the embodiments can be improved as compared with the conventional curative effects.

According to the preferred embodiments, since the sound pressure sampling is performed at a shorter cycle then by which a biological body feels in substantially real time, the electric stimulus can be modulated in substantially real time with the hearing stimulus, so that unpleasant feelings are removed and the curative effects to reduce pain can also be improved.

In addition, according to the first and second embodiments, the frequency of the electric stimulus signal is selected to be at a low frequency, for instance, 0 to 60 Hz, so that the mental physical attributes of a biological body can be relaxed—by a pulling phenomenon against the natural vibration of automatic nerve (for instance, in the phenomena of "KEDACHI (goose flesh)" and "FURUE (tremble)"—to present cool feeling for the biological body, the natural vibration being approximately 15 Hz.

According to the method of generating a low frequency electric stimulus signal of a third embodiment, in response to a waveform of sound information derived from a sound source, at least one of the controls of the current and voltage is performed to modulate the electric stimulus signal at a rhythm. The frequency of the electric stimulus signal is selected to be at a low frequency.

In the preferred embodiment of the third embodiment, first, a judgment is made on whether or not sound information is present. If this sound information is present, only low frequency information having a frequency lower than approximately 200 Hz is derived.

As a result of the detection, when no sound information is detected, the quasi-sound information having the arbitrary waveform is generated from a rhythmic generator which is independently provided. The control of the current or voltage is performed by utilizing the respective waveforms of these low frequency sound information and quasi-sound information.

In accordance with the preferred embodiment of the third embodiment, it is preferable that the intensity of the electric stimulus signal is selectively adjustable based upon the information supplied from the external source.

According to the low frequency electric stimulus signal generating apparatus of the fourth embodiments an input section for setting conditions and for adjusting the same, and a stimulus signal generating section is included; the stimulus signal generating section including: a waveform control section for outputting a rhythmic-modulated waveform signal by deriving low frequency sound information from a sound source, a current control section for generating a current controlled stimulus signal based upon the rhythmic-modulated waveform signal, a voltage control section for generating a voltage controlled stimulus signal based upon the rhythmic modulated waveform signal, a control system selecting section for outputting at least one of the current stimulus signal or the voltage stimulus signal as the electric stimulus signal, and a control section for controlling operations of the control sections and selection based upon a signal derived from the input section.

For the fourth embodiment, the waveform control section includes a comparator for detecting whether or not sound information is present, a low pass filter for filtering low frequency sound information only having a frequency lower than approximately 200 Hz, a rhythmic generator for generating quasi-sound information, and a selection switch for selecting the low frequency sound information when the sound information is input, and the quasi-sound information when the sound information is not input.

In the fourth preferred embodiment of the invention, the current control section includes an intensity setting circuit of the rhythmic-modulation waveform signal, and a current stimulus signal generating circuit for outputting a current stimulus signal having the same waveform as that of a waveform input from the intensity setting circuit, and further the voltage control section includes a voltage stimulus circuit for outputting a voltage stimulus signal by adjusting the rhythmic-modulated waveform signal.

In the preferred embodiment of the fourth embodiment, the intensity of the electric stimulus signal is selectively adjustable.

In the low frequency electric stimulus signal generating apparatus according to the third and fourth embodiments, either the control of the current, or the voltage is performed based upon the waveform of the sound information so as to irregular modulate the electric stimulus signal. As a result, a biological body can be electrically stimulated, i.e., being provided percutaneous stimulus in accordance with the tempo of the music etc. When there is no sound information, the biological body can be stimulated by the waveforms of the quasi-sound information which has been generated in the quasi-sound production. Consequently, since the biological body can be stimulated with the percutaneous stimulus at the rate at which he can feel it in substantially real time, the pain reduction and curative effects can be more improved, as compared with the conventional musical medical treatment.

Furthermore, according to the third and fourth embodiment, since the sound information containing only the low frequencies (lower than about 200 Hz) of the base and drum is utilized, the unpleasant feelings can be effectively eliminated.

According to the low frequency electric stimulus signal generating apparatus of the fifth embodiment which comprises a stimulus signal generating section which includes a control section in which sound volume levels supplied from a sound source are sampled at a rate at which a biological body feels it in substantially real time, each of the sampled volume levels is converted into a corresponding amplitude control value and the resultant value is output, and predetermined control information is output, and a current/voltage control section for performing an amplitude modulation in response to the amplitude control value within a range of 0 to 100% of an initial set amplitude value of current and voltage stimulus signals.

To embody the fifth embodiment, the stimulus signal generating section includes a control system selecting section for switching only one of the current and voltage stimulus signals based upon control information derived from the control section and for outputting the same as the electric stimulus signal.

In the preferred embodiment of the fifth embodiment, the current control section includes a waveform generating section for outputting a voltage waveform having an arbitrary frequency, an intensity setting circuit for controlling an intensity of the voltage waveform signal by the amplitude control value, and a current stimulus signal generating circuit for outputting a current stimulus signal having the same waveform as that of the voltage waveform signal input from the intensity setting circuit.

In the preferred embodiment of the fifth embodiment, the voltage control section includes a waveform generating section for outputting a voltage waveform signal having an arbitrary frequency, and a voltage stimulus signal generating circuit for controlling an intensity of the input voltage waveform signal based upon the amplitude control value and for outputting the same as a voltage stimulus signal.

In the fifth preferred embodiment of the invention, the frequency is selected from 0 to 60 Hz.

In the fifth preferred embodiment of the invention, the sampling operation is performed within a time period from 0.01 to 0.5 seconds.

Furthermore, in the fifth preferred embodiment of the invention, the control section includes means for subdividing the sound volume levels into a plurality of level steps, and means for converting the subdivided levels into the corresponding amplitude control values and for outputting the converted control values.

Moreover, in the fifth preferred embodiment of the invention, the electric stimulus signal having 24 steps is obtained as the amplitude control value within a range from 0 to 100% of the initial setting intensity.

In accordance with the fifth embodiment, the control of current or voltage is performed based upon the sound pressure level of the sound information so as to irregularly the electric stimulus signal. Accordingly, a biological body can be stimulated by electric stimulus in response to the tempo of the sound information. Also, no stimulus time period can be made with the hearing stimulus when the music is in rest condition, or the sound volume level is low. As a result, percutaneous stimulus is provided to the biological body at the timing at which the biological body feels in substantially real time, and thus the curative effects of the musical cure according to the invention can be improved as compared with the conventional curative effects.

According to the preferred embodiments, since the sound pressure sampling is performed at a shorter cycle by which a biological body feels in substantially real time, the electric stimulus can be modulated in substantially real time with the hearing stimulus, so that unpleasant feelings are removed and the cure effects to reduce pain can be also improved.

In addition, according to the fifth embodiment, the frequency of the electric stimulus signal is selected to be a low frequency, for instance, 0 to 60 Hz, so that the mental physical matters of a biological body can be relaxed by a pulling phenomenon against the natural vibration of automatic nerve (for instance, in the phenomena of "KEDACHI (goose flesh)" and "FURUE (tremble)" to present cool feeling of a biological body, the natural vibration is approximately 15 Hz.

According to the low frequency electric stimulus signal generating method of the sixth embodiment, the control information previously stored in the control section is read out and the alternating stimulus of the current and voltage is applied to a biological body without utilizing the sound information derived from the sound source. In this case, the above sound information derived from the sound source is only used for the hearing stimulus.

To embody the sixth invention, the control information is selected from more than one sort of the waveform, frequency and intensity information. The control information is selectable and variable to proper values suitable for a biological body in response to the external input.

Moreover, for the sixth embodiment, the alternating operations of the current and voltage stimulus signals are performed at random.

The time interval between the succeeding alternating operations is preferably settable at random within a range from several seconds to several tens of seconds. In particular, the alternating time interval is preferably selected to be approximately 2 seconds to 1 minute.

Furthermore, the frequency of the electric stimulus signal employed in the sixth embodiment is selected to be a low frequency signal having the frequencies from 0 to 60 Hz.

According to the low frequency electric stimulus signal generating apparatus of the seventh embodiment, an input section for setting conditions and for adjusting the same, and a stimulus signal generating are included. The stimulus signal generating section includes: a control section for previously storing control information which is readily accessible; a current control section for generating a current stimulus signal controlled by the control information, a voltage control section for generating a voltage stimulus signal controlled by the control information, and a control system selecting section for alternately switching the current stimulus signal and the current stimulus signal and the voltage stimulus signal based upon the control signal so as to output the same as the electric stimulus signal.

For the seventh embodiment, the control information of the current and electric stimulus signals is selected from more than one sort of waveforms, frequencies and intensity, and the control information is selectable and variable based upon external input.

In a preferred seventh embodiment, the alternating selection of the current and voltage stimulus signal is performed at random.

Furthermore, in the preferred seventh embodiment, a time interval of the alternating selection of the current and voltage stimulus signals is set at random within several seconds to several tens of seconds.

However, in a preferred embodiment, a frequency of the electric stimulus signal is selected from a low frequency of 0 to 60 Hz.

In accordance with the low frequency stimulus signal generating method according to the sixth and embodiments seventh, the control of the current or voltage is performed based upon the waveforms of the sound information so as to irregularly the electric stimulus signal. Accordingly, the frequency, waveform, and intensity of the sound information of the favorable music are previously stored, so that a biological body can the electric stimulus (percutaneous stimulus) in response to the tempo of this favorable music. As a result, the percutaneous stimulus can be applied to a biological body at predetermined timing at which he can feel this stimulus in substantially real time, with the result that higher curative effects than in the conventional musical curative method can be expected according to the present invention.

In addition, according to the sixth and seventh preferred embodiment, the current control system and the voltage control system are alternately switched to give the alternating stimulus to a biological body, with the result that it is possible to avoid not having a biological body feel no stimulus upon receipt of the electric stimulus, and therefore the unpleasant feeling can be eliminated, the pain effects can be reduced, and the curing effects can be improved.

In order that these inventions may be more clearly understood, preferred embodiments will be described, by way of example, with reference to the accompanying drawings.

BRIEF DESCRIPTION OF THE DRAWINGS

FIGS. 2A and 2B are block diagrams, each of which shows a portion of detailed block diagram of a low frequency electric stimulus signal generating apparatus to explain the present invention;

FIGS. 3A to 3K are voltage waveform signal diagrams for explaining the present invention;

FIG. 4 is a schematic diagram for explaining a table conversion;

FIG. 5 is a functional block diagram of a CPU;

FIGS. 6 to 14 are flowcharts of the operations according to the preferred embodiments of the present invention.

FIG. 15 is a block diagram of the current stimulus signal gen. c/ct.

FIG. 16 is a block diagram of a c/ct. for simply amplifying the input voltage.

DETAILED DESCRIPTION OF THE PREFERRED EMBODIMENT

General Description

Figure 1:
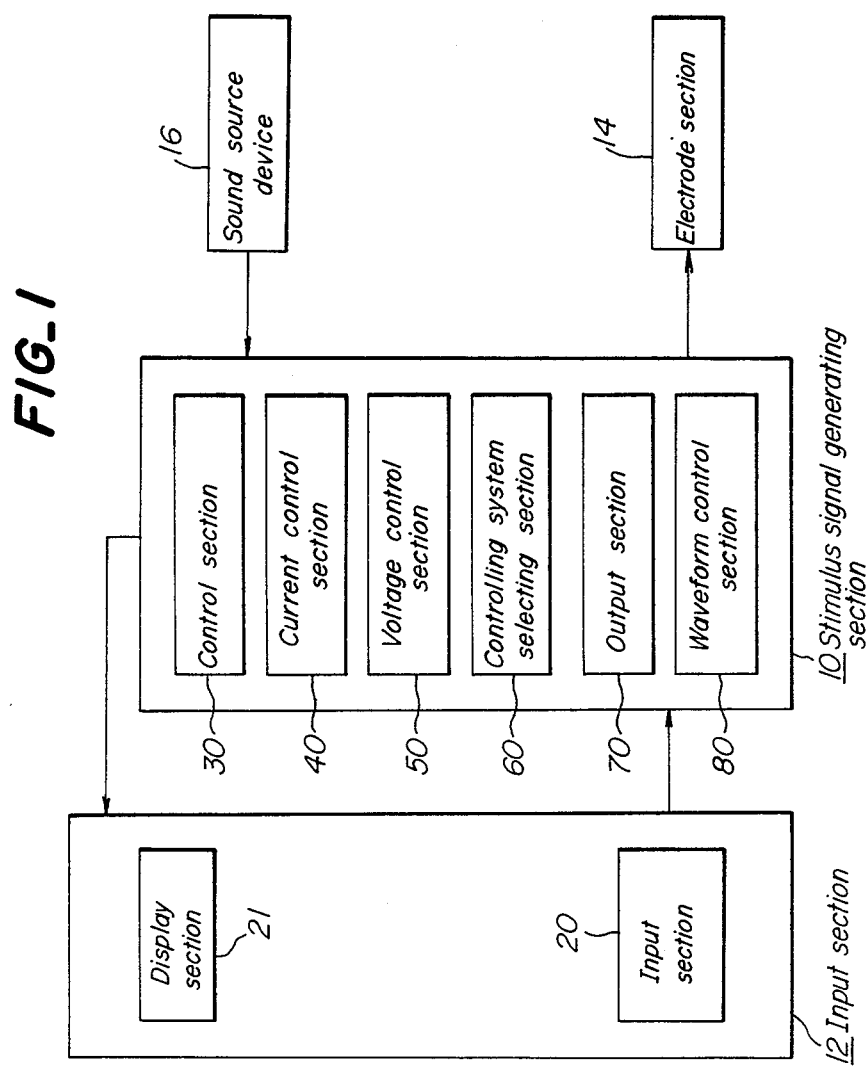
FIG. 1 is a block diagram illustrating a basic arrangement to explain the present invention.

FIG. 1 is a block diagram illustrating a basic arrangement to explain the present invention. FIGS. 2A and 2B are block diagrams each of which illustrates a portion of a detailed block diagram of a low frequency electric stimulus signal generating apparatus to explain the present invention. In FIGS. 2A and 2B, portions shown by the same reference marks a, b, c, d, e, f, g, h, i, and j should be connected to each other.

Referring now to FIG. 1, there is shown a low frequency electric stimulus signal generating apparatus that basically includes a stimulus signal generating section 10 for generating the low frequency electric stimulus signal, a host section 12 for selectively supplying data which are required to drive the stimulus signal generating section 10, and an electrode section 14 for applying the electric stimulus signal generated to biological bodies or living body.

Description of Basic Construction

In the preferred embodiment, the host section 12 mainly includes an input section 20 for inputting various types of signals to the stimulus signal generating apparatus 10. These signals are to set the initial conditions, predetermined conditions, to adjust the proper conditions, or to initialize the generation of the electric stimulus signal. The above-described predetermined conditions include, for instance, amplitudes (intensity), waveforms, frequencies, stimulus patterns, controlling systems for controlling current or voltage, and selection of electrodes. In addition, if required, this host section 12 further includes a sound source device for generating music and so on, an electric converting devices, such as a speaker or earphone for reproducing the acoustic information originated from the sound source device, or a display section 21 for visually displaying the generated electric stimulus signals. Alternatively, instead of providing these sound source devices to the host sections 12, they may be connected, as an outer source device, to the stimulus signal generating section 10, as indicated by reference numeral 16.

In the present embodiment, the stimulus signal generating section 10 employs the current or voltage control system. According to this system, the volume of sound level supplied from the sound source device 16 is detected, and the physical quantities of the current, or voltage stimulus signals such as frequencies, amplitudes (intensity) or pulse are controlled in response to the detected volume levels, while these electric stimulus signals are continuously modulated, thus modulated electric stimulus signals are output from the stimulus signal generating section 10. In this case, the electric stimulus signals are preferably selected in such a manner that the frequency of the stimulus signals is a low frequency within the present frequency range of approximately 0 to 50 Hz, at which biological bodies such as patients who use this low frequency electric stimulus signal generating apparatus, feel pleasant. To this end, the stimulus signal generating section 10 mainly includes a control section 30 having a CPU (central control unit) for converting the volume level for controlling the physical quantities into predetermined controlling quantities, and for controlling other desired controls; a current control section 40 for controlling the current in response to the above-defined controlling quantities; a voltage control section 50 for controlling the voltage in response to the above-defined controlling quantities; a controlling system selecting section 60 for selecting either the voltage stimulus signal generated from the voltage control section 50, or the current stimulus signal produced from the current control section 40; and an output section 70.

Moreover, in the preferred embodiment, this stimulus signal generating section 10 includes a waveform control section 80 for performing rhythmic stimulus (also referred to as "rhythmic modulation") by controlling the rhythm of the electric stimulus signal in such a manner that the waveforms of both the current and voltage are controlled by the sound waveform having less than approximately 200 Hz during presence of the sound, and by the quasi-sound waveform produced during absence of the sound independent of the volume level.

In addition, according to the preferred embodiment, the control section 30 includes means for generating various control signals for waveforms, pulse widths, frequencies, intensity (amplitudes) and changing over as parameters to stimulate biological bodies in order to alternately change, at random, the current control system, or voltage control system, independent of music, acoustic information and so on. As will be discussed later, the pattern of the current, or voltage stimulus signal is preset by this control means to the stimulus pattern suitable for the respective biological bodies.

Detailed Description of Arrangements

Referring now to FIGS. 2A and 2B, a description will be made of the arrangements and also the controlling system. It should be noted that the same reference numerals will be employed for the same circuit arrangements as those shown in FIG. 1. In addition, since the below mentioned arrangements and controlling system are merely example, the present invention is not obviously limited to those.

Description of Block Diagram

In FIGS. 2A and 2B, the acoustic information from the sound source device 16, e.g., radios, televisions and other acoustic devices, is transferred via an amplifier 90 to a sound volume-to-DC level converter 91. The resultant volume level signal is sent to an A/D (analogue-to-digital) converter 92.

The output of the amplifier 90 is, on the other hand, transferred to an electric-acoustic converter 95 such as a speaker, or an earphone, via an electronic volume 93 which can be adjusted by an external switch SW, and an amplifier 94. Then, this output is reproduced and provided to the biological body as hearing stimulus. It should be noted that this sound reproduction system is not necessarily employed in this electric stimulus apparatus, but may be substituted by the reproduction system of the external sound source apparatus 16.

The output of the amplifier 94 may be displayed by the light emitting display section 23 in such a manner that variations in the acoustic information are displayed. In this case, this output is processed in a DC converter 22 of the display section 21 and the display section is made of an LED (a light emitting diode). It should be also noted that the light emitting display section 23 may be provided within the host section 12.

In the preferred embodiment, the control section 30 includes:

a series interface for receiving the signal sent from the input section 20 of the host section 12 by way of a wireless or wire system;

a CPU 32 for performing various process in response to the signal from this interface 31;

a RAM (random access memory) 33 for reading and writing data required for performing the various process in CPU 32;

a ROM (read only memory) 34 for reading out the necessary data which have been previously stored, therefrom, for the process in the CPU 32;

a PTM (programmable time unit) 35 for automatically outputting arbitrary frequencies as an internal clock with respect to the data set by the CPU 32;

an output port 36 for outputting the outputs containing various control signals from the control section 30 to other circuit arrangements; and an input port 37 for receiving an input to the control section 30, e.g., a signal to detect the end of one cycle of the frequency from the PTM 35.

A portion of the output derived from the output port 36 is supplied as a control signal to a pulse number generator 96, and a changing switch 97 for changing the signals from PTM 35 and the pulse number generator 96.

In the preferred embodiment, both the current control section 40 and the voltage control section 50 commonly employ a waveform generating section 41 and a waveform selecting section 42 constructed of, for instance, an electronic switch for selectively deriving the generated voltage waveform. To a frequency clock section 43 of this waveform generating section 41, a frequency, or pulse number control signal is transferred via the changing switch 97, and the frequency control signal from the output port 36 is supplied. Moreover, data for changing the pulse width of the voltage waveform to be generated is transferred to a pulse width data section of the waveform generating section 41.

In the waveform generating section 41, there is provided a waveform generating circuit 45. This waveform generating circuit 45 employs many circuits from which various types of voltage waveform signals can be output, as illustrated in FIGS. 3A to 3K. The frequency of the voltage waveform signal can be controlled by a signal from the frequency clock section 43, and furthermore, the width of the signals can be varied by the data from the pulse width data section 44. It should be noted that such waveform generating circuit 45, frequency clock section 43 and pulse width data section 44 can be easily fabricated by utilizing the conventional electronic circuit techniques, and therefore by employing no specific electronic circuit. At least one or more than two waveform generating circuit 45 are operated to select one, or more than two sets of the voltage waveform patterns in response to the control signal derived from the output port 36 as a waveform select signal. Also, the waveform generating section 41 is so designed that one or more than two sets of the voltage waveform patterns output from the waveform generating section 41 can be derived based upon a waveform select signal from the output port 36. The circuit arrangement of the waveform selecting section 42 may be also manufactured by employing the conventional circuit techniques, and requires no specific circuit arrangement.

One of the voltage waveform signals selected by this waveform selecting section 42 is supplied to a current stimulus generating circuit 47 via an intensity (amplitude) setting circuit 46 of the current control section 40. The other of the voltage waveform signal is supplied to a voltage stimulus generating circuit 51 of the voltage control section 50.

In the current control section 40, the voltage waveform signal input into the intensity setting circuit 46 is properly set to a voltage waveform signal having a suitable amplitude in response to the control signal from the output port 36, whereas in the current stimulus generating circuit 47, its input voltage waveform pattern is converted into a current waveform type electric stimulus signal having the same pattern as the voltage waveform pattern.

In, on the other hand, the voltage control section 50, the voltage waveform signal input into a supply voltage stimulus generating circuit 51 via the waveform selecting section 42, is converted into a voltage waveform type electric stimulus signal having a proper intensity and a proper frequency in response to an intensity (amplitude) and frequency control signal from the output port 36.

In addition, in the preferred embodiment, there is a controlling system selecting section 60 for selecting the electric stimulus signal produced in accordance with either the current control system, or the voltage control system, and for supplying the selected electric stimulus signal to a biological body as skin stimulus. This selecting operation can be performed in response to a selecting system control signal derived from the output port 36, whereby either the current control system, or the voltage control system is selected, otherwise, both control system are alternately selected.

The electric stimulus signal obtained via this controlling system selecting section 60 is transferred to an output section of the low frequency electric stimulus signal generating apparatus. To this output section 70, electrodes for applying skin stimulus to more than one portion of the biological body are connected. A selection of the electrodes is under the control by means of an electrode selection controlling signal derived from the output port 36.

In the preferred embodiment, the waveform control section 80 includes: means for detecting acoustic information from the amplifier 90, for instance, a comparator 81; a low-pass filter 82 for passing therethrough the acoustic information having the frequency lower than approximately 200 Hz; a rhythm generator 83 for generating quasi-acoustic waveform during a rest period of the acoustic information; and a selection switch 84 for selecting the acoustic information having the frequency lower than approximately 200 Hz supplied from the low-pass filter 82 when the acoustic, or sound information is detected by the comparator 81, and for transferring the quasi-acoustic information as a rhythm-modulated (stimulus) waveform to the waveform selecting section 42 when the comparator 81 detects no acoustic information. The above-described acoustic information is, on the other hand, transferred via an A/D converter 92 to the control section, and is displayed as rhythmic illustration at the display section 21 under the control of the control signal from the output port.

CONTROLLING SYSTEM FOR PRODUCING ELECTRIC STIMULUS SIGNAL

In the present invention, the frequency of the electric stimulus signal for achieving the skin stimulation is selected to be at a low frequency. In the preferred embodiment, a frequency range is determined to be at approximately 0 to 60 Hz at which a biological body feels pleasant. By controlling either the current or the voltage in accordance with the sound volume level of the sound source, the electric stimulus signal is modulated.

In case of controlled current, cells of a biological body feel electric charges as an energy, whereas in case of controlled voltage, small current is sufficient if the body feels the same pleasantness as that in the current controlling system because the voltage fluctuates. It is known in the art that according to both controlling systems, a biological body can have specific pleasant feelings.

In the preferred embodiment, the following three modulating systems are performed.

1. The electric stimulus signal is modulated by controlling the frequencies of the current and voltage, amplitude and pulse number, in relation to the sound level.

2. The electric stimulus signal is rhythmic-modulated by controlling the current and voltage while using properly sound waveforms and quasi-sound waveforms having a frequency lower than about 200 Hz, without utilizing the sound level.

3. The electric stimulus signal is stimulus pattern-modulated by controlling the current and voltage patterns based upon the combination of various control information (waveforms, frequencies and amplitudes) which is previously set in the control section, without using the sound information.

Referring now to FIGS. 4 to 16, a detailed description will be made. FIG. 4 is a schematic diagram for explaining a table conversion. FIG. 5 is a functional block diagram of CPU 32. FIGS. 6 to 14 are flowcharts of the operations according to the preferred embodiment, where the respective processing steps are indicated by "S".

[I] Use of Sound Level Frequency Modulation

First, a power switch is turned on to energize the music source device 16. Thus, acoustic information such as music is produced, thereby providing hearing stimulation to a biological body such as a patient.

The acoustic, or sound information originated from the music sound device 16 is converted into a sound level composed of a data of a suitable number of bits, such as, for example, an 8-bit data or 256-bit data, as illustrated in the upper column of FIG. 4, by utilizing a sound volume-to-DC level converter 91 and an A/D converter 92 in real time processing.

By the input section 20 of the host section 12 (e.g., input key), predetermined initial information containing the modulation, waveform, frequency, electrode selection, controlling system and so on is input to the control section 30 of the stimulus signal generating section 10. Based upon this initial information, the processing is performed by the setting means of CPU 32 (S1), and corresponding control information is read out from ROM 34, or converted into predetermined control information. Thereafter, the above-described control information is supplied to the respective circuit arrangement components of the output port 36 to set the initial conditions (S2).

For instance, a waveform select signal is transferred to a waveform generating section 41 to actuate the waveform generating circuit 45, while this control signal is sent to the pulse width data section 44 so as to initial-set the proper pulse width.

When the initial frequency information is set to the frequency clock section 43, the frequency of the voltage waveform signal from the waveform generating circuit 45 is initially in such a manner that a biological body feels the maximum stimulation, for instance, 30 Hz, when the waveform of the electric stimulus signal is the same. This initial setting of the frequency is set independent of presence of the sound information supplied from the music sound device 16.

Simultaneously, the control signal is supplied to the voltage controlling and current controlling system selecting section 60 in order to select either controlling system, thereby determining the corresponding electric stimulus signal.

The intensity of these electric stimulus signals is set every time the control signal read out from ROM 34 is transferred to an intensity setting circuit 46 and a voltage stimulus generating circuit 51 in accordance to the selection by the input section 20. This intensity of the electric stimulus signal can be adjusted until a user feels pleasant while receiving this electric stimulus signal.

When this stimulus intensity becomes a proper level, the start input is transported to the control section 30 by turning on the start key of the input section 20 in the host section 12, the medical treatment commencement data is sent to the stimulus signal generating section 10 (S3) while it is processed in CPU 32, and then, the control section 30 starts to receive the volume level from the A/D converter 92(S4). This signal reception is carried out by the sampling operation of CPU 32. The respective volume levels are once written into RAM 33, which have been acquiring every sampling operation (S5), and are sequentially read out from RAM 32, if required (S6). The volume level of data of suitable bit numbers such, for example, as the 8-bit data or 256-bit data is converted in CPU 32 into 16-stepped level data (S7).

In this level conversion, not only the zero volume, but also the lower volume are recognized as the electric stimulus signal having the zero level intensity, which forcibly correspond to the zero step. The 16-step volume levels are converted into the corresponding frequencies for the lower frequency region (step 8). According to this level conversion, the conversion frequencies corresponding to the respective volume levels are previously stored in ROM 34 in the table form, and thus, the corresponding frequency is read out by comparing it with the frequency conversion table for every volume level (S8). This frequency information is sent via the output port 36 to the corresponding circuit arrangement (S9). In this case, the period of the sampling is preferably selected to be in a range from approximately 0.01 to 0.5 second, for example, at which a biological body feels practically in real time. Also, at the frequency table, the stimulus frequencies from 0 to 60 Hz are allocated to the 16-step volume levels, as illustrated in FIG. 4, at which a biological body feels comfort, or pleasantness. The frequencies of the stimulus signal are preferably selected to a range from 0 to 30 Hz. As is easily understood from FIG. 4, the volume level "0" is set to 1.5 Hz, the level "1" is set to 2 Hz, the level "5" corresponds to 5 Hz, the level "10" is equal to 10 Hz, the level "11" is selected to be 15 Hz,—, the level 15 is selected to be 30 Hz. Under this frequency conversion scheme, CPU 32 includes conversion means 102 for performing the frequency conversion by the sampling operation (see FIG. 5).

When the volume level is frequency-converted and output from the output port 36 every sampling periods, this frequency is supplied to the frequency clock section 43 of the waveform generating section 41 and the voltage stimulus generating circuit 51, whereby the frequencies which have been initially set are sequentially updated by the frequencies newly converted from the received volume level. Under such condition, the current, or voltage frequency converting operation is effected, so that the frequency modulation of the electric stimulus signal can be automatically achieved.

As previously described, music and sounds are utilized as hearing stimulus, the sound volume level supplied from the sound source device 16 is sampled in substantially real time in synchronism with the hearing stimulus, and the frequency of the electric stimulus signal is modulated to the frequency corresponding to the sound volume level at the same time as the sampling time, according to the invention, whereby this electric stimulus signal is applied to a biological body as skin, or percutaneous stimulus.

The most important aspect of such a frequency modulation is to substantially perform the real-time sampling, and also to set the electric stimulus (corresponding to the percutaneous stimulus) in response to this sampling operation. In the preferred embodiment, when the sound volume (sound pressure) level is equal to zero, or very low level (i.e., less than one sixteenth (1/16) of the maximum level), the frequency is set to, for instance, less than 1.5 Hz. Under such circumstances, the waiting time period for the succeeding stimulus is preset as follows. For instance, at the 1 Hz frequency, the waiting time period is 1 second; at the 0.5 Hz frequency, the waiting time period is 2 seconds; at the 0.25 Hz frequency, the waiting time period is set to 4 seconds. As a result, according to the conventional music, no percutaneous stimulus is performed in case of the rest time and lower sound volume. Since the stimulus time of this percutaneous stimulus is, practically, not synchronized with any stimulus time period of the hearing stimulus, cerebrum cortex of the biological body feels no pain because the stimulated nerves improve the effects of cure.

In the meantime, when the waiting time period for the subsequent percutaneous stimulus becomes long, there may be instances where generation of the electric stimulus signal does not reflect the hearing stimulus. To avoid such a problem, in the preferred embodiment, the control section 30 of the stimulus signal generating section 10 includes frequency forcibly converting means 103 for forcibly converting the input signal into a new frequency corresponding to the newly sampled volume level when the waiting time period becomes longer than a predetermined level, while continuously watching the converting frequency and the sound volume level.

Operation flows of the frequency forcibly converting means 103 will now be described with reference to FIG. 8.

At first, a judgement is carried out on whether or not the sampled volume level is lower than one sixteenth of the maximum level (S10). If the answer is NO, another judgement is performed whether or not the present frequency is lower than, for instance, 5 Hz (S12). If the answer is YES, that is, if the sound volume level is lower than one sixteenth of the maximum level, the cure intensity is set to the zero step (S11). Then, if the frequency is higher than 5 Hz, a judgement is made on whether or not one cycle of this frequency is completed (S13). If one cycle of the frequency is not yet completed, the cure intensity is set to the setting intensity (i.e., the initial setting intensity) (S16). When one cycle of this frequency of this frequency is accomplished, the volume level is converted into the frequency corresponding to the volume level which has been acquired in the succeeding sampling operation (S15). The resultant signal is output via the step S16. When the present frequency is lower than 5 Hz which has been judged in the above step S13, it is compared with the sound volume level obtained at the sampling operation just before the present sampling operation (S14). If the present volume level is higher than the previous volume level, it is forcibly set to the frequency corresponding to the present volume level during the signal process in the step S15, and thereafter processed in step S16 to output the resultant signal. To the contrary, if the present volume level is lower than the comparision level, the process of the step S16 is carried out. The above-described overall signal process is continuously performed during the operation of the electric stimulus signal generating apparatus. It should be noted that although the converting means 102 and the frequency forcibly converting means 103 are separately employed in the preferred embodiment, the frequency forcibly converting means 103 may be assembled in the converting means 102. In addition, the operation flow is not limited to the above-described flow.

Amplitude Modulation

At first, initialization is similarly performed as it is effected in the frequency modulation (see FIGS. 5 and 6). In this embodiment, the initialized intensity corresponds to the maximum intensity by which a biological body feels maximum stimulus. This initialized intensity is equal to a set intensity which is written in RAM 33 and read therefrom, if required.

When, for example, an 8-bit data sound volume level is sequentially taken in by the sampling operation, the set intensity is sequentially updated in real time by another intensity (amplitude) corresponding to the above sound level in a range from 0 to 100 percent (0–100%). As a result, the amplitude modulation for the electric stimulus signal can be achieved, whereby the intensity modulation for the percutaneous stimulus can also be achieved. This amplitude (intensity) conversion is continuously performed.

This amplitude modulation is mainly performed by employing the cure intensity setting means 104.

Referring now to FIG. 9, the amplitude modulation process will be described. First, the set intensity is read out from RAM 33 (S20), and secondly, the 8-bit volume level is read out from the RAM 33 (S21). Subsequently, to execute the following equation (I), the 8-bit data of this volume level is divided by 256, and the resultant quotient is multiplied by the set intensity to obtain the cure intensity, that is to say, an amplitude control value (S22). It should be noted that the calculation process is not limited to the above process.

$$\text{The cure intensity} = (\text{the set intensity}) \times \{(\text{the 8-bit data of the sound volume data})/256\} \quad (I).$$

In this case, the 24 level steps of intensity of the electric stimulus signal is preferably obtained as the amplitude control value, which is set within a range from 0 to 100 percent. Also, when the music, sound volume level is equal to zero, or very low, the electric stimulus signal intensity is forcibly set to zero. However, the intensity becomes low when the sound volume level is low, even if this intensity is not set to zero. As a result, a biological body feels no stimulus so that the body feeling is adapted to music and sounds.

In the preferred embodiment, the calculation process was accomplished in the functional block of the cure intensity setting means 104. It is also possible that the cure intensity (i.e., amplitude control value) is stored as the conversion table in ROM 34, and this conversion table is read to convert the data into the cure intensity.

The resultant amplitude control value is output from the output port 36, and then transferred to the intensity setting circuit 46 and the voltage stimulus generating circuit 51, where the amplitudes of the current and voltage stimulus signals are modulated. In this case, either the current control system, or the voltage control system, is selected by the control system selecting section 60 in the same way as the frequency modulation system.

In accordance with this amplitude modulation, the sound volume level supplied from the sound source device is sampled in substantially real time as the hearing stimulus, and amplitude-converted at the same time as the sampling time, so that the amplitude of the electric stimulus signal is set within a range from 0 to 100 percent of the set intensity in real time.

The main feature of the present amplitude modulation is to supply no electric stimulus when the music sound is in a rest condition and the sound volume is low. That is to say, no stimulus signal of the percutaneous stimulus can be produced in accordance with the music, which causes great curing effect in the music curing method.

Pulse Number Modulation

In this modulation system, the initialization is carried out the same way as in the frequency modulation system. Instead of the frequency, a pulse having a pulse rate of, for instance, 16 pulses/second (corresponding to 30 Hz) is produced from the pulse number generator 96 (FIGS. 5 and 6).

Then, when the 8-bit data of the volume level is sequentially read out, it is sequentially updated in real time by the pulse numbers corresponding to the read volume level within a range of the initialized set pulse number as a maximum pulse number, so that the control of the electric stimulus signal can be achieved, and thus the pulse number control of the percutaneous stimulus can be achieved. This pulse number modulation is continuously performed in the preferred embodiment.

This pulse number modulation is mainly performed by employing pulse number setting means 105 of CPU 32.

In accordance with the pulse number modulation process (see FIG. 10), the sound volume level subdivided into 16-stepped levels is read out from RAM 33 (S23), and then the corresponding pulse-number-converted value is obtained in ROM 34 by the table conversion (S24). Subsequently, the following equation (II) is calculated (S25).

Pulse number control value=(16-stepped converted values)−1  (II)

In the preferred embodiment, the pulse number control value is calculated based upon the equation (II), and thereafter sent via the output port 36 to the pulse number generator 96. Accordingly, the pulse is generated at the pulse rate corresponding to the sound volume level which has been sampled, and transferred via a changing switch 97 to the frequency clock section 43 in the waveform generating section 41. As a result, the current and voltage stimulus signals can be produced as the pulse signal, the pulse rate of which is controlled. The pulse numbers employed in the preferred embodiment are preferably set to the range from 0 to 30 pulses/second at which a biological body feels pleasant.

According to the above equation (II), the pulse number becomes zero when music is in the rest condition and the sound volume is low.

It should be noted that the calculation of the pulse number control value is not limited to the above-defined equation (II), but may be realized by other different calculation methods. Instead of the equation calculation, the pulse number control value corresponding to the sound volume level is previously stored in ROM 34, and then, the necessary data may be obtained from ROM 34 by way of the table conversion.

As has been described in the above preferred embodiment, the percutaneous stimulus can be applied to a biological body with the hearing stimulus in substantially real time by employing the pulse number modulation, in the same way as the frequency modulation.

[II] Non Use of Sound Volume Level

RHYTHMIC MODULATION

Referring now to FIG. 11, a rhythmic modulation process will be described. The setting conditions such as the modulation system, waveform, stimulus pattern, control method, and electrode selection are input into the control section 30 from the input section 20 of the host section 12 as curing data. This processing will be described. Just like the above frequency modulation and other modulations, the initial data setting is performed based upon these setting conditions. To feel with sufficiently stron intensity, the waveform having a great amplitude is employed while the initial setting is effected. For example, when a biological body starts to feel, as optimum stimulus, the stimulus pattern, the medical treatment will be commenced. At first, the rhythmic modulation command information is sent from the output port to the waveform control section 80 by the modulation system setting means 106 of CPU 32, so as to enable this waveform control section 80 (S30). A judgement is made on whether or not the sound information supplied from the sound source device 16 is present (S31). When the output is present, it is compared by the comparator 81 with, for instance, a level, and the selection switch 84 is changed over to the low pass filter 82 so as to send the sound information lower than approximately 200 Hz to the waveform selecting section 42 as the rhythmic modulation waveform (S32). When, on the other hand, no sound information is present (S33) they, in response to the command sent from the modulation system setting means 106, the waveform selection 42 is changed to select only the rhythmic-modulated waveform, which is sent to the succeeding stage (S34).

The rhythmic-modulated waveform is sent from this waveform selecting section 42 to the voltage stimulus generating circuit 51, and also to the current stimulus generating circuit 47 via the intensity setting circuit 46 (S32). Based upon both the rhythmic-modulated waveform, the rhythmic and/or intensity of the current and voltage stimulus signal is controlled (S33), and output as the electric stimulus signal in accordance with either the current, or voltage controlling system, in the same way as the above-described modulation systems. As a result, rhythmic and intensity stimulus can be applied to a biological body.

In the preferred embodiment, the reason why the low pass filter has a pass band lower than approximately 200 Hz to adapt the stimulus obtained by the base and drum sounds to the stimulus which is achieved by the frequency pattern within the above frequency range.

By receiving such rhythmic stimulus, unpleasant feeling of the biological body can be relaxed or mitigated, or cured.

[III] Stimulus Pattern Modulation Without Employing Sound Source Device

ALTERNATELY CHANGING CURRENT OR VOLTAGE CONTROL SYSTEM

In the preferred embodiment, the parameters for stimulus patterns selected by the control section 30 are automatically varied with no reaction to music. These parameters typically contain waveforms pulse widths, frequencies and intensities.

In the present embodiment, two examples where the frequencies and intensities are used as variable parameters, are described for the stimulus pattern modulation processing with reference to FIGS. 2, 5 and 12.

First, the initial setting values and also the variable parameter values for the frequencies and intensities have been previously stored in ROM 34, respectively.

(1) Frequency Variable in Stimulus Pattern Modulation Processing

In response to commands sent from the input section 20, the stimulus parameter modulation is designated by a modulation system setting means 106, the same as in the previous modulation system (S40). Then, the initial settings for the waveform, pulse width and intensities are performed by the setting means 101 (S41). Thereafter, in response to this command, stimulus parameter setting means 107 is actuated to read out the frequencies from ROM 34. These frequencies are output via the output port 36 to the waveform generating section 41 and voltage stimulus generating circuit 51 (S42). These frequencies may be fixed values, or variable at random. Thereafter, the electric stimulus signal is similarly controlled as in the previous frequency modulation (S43). Subsequently, based upon this modulation system selected by the above-described modulation system setting means 106, the command for the alternately outputting the current and voltage stimulus signals at a constant rate, or random rate, is given to the control system selecting section 60 by this setting means 106. Accordingly, these stimulus signals are alternately output (S44), which enables the voltage and current stimulus to be alternately applied to a biological body.

The above alternate selection can be performed by the command from the input section 20, and the stimulus signals are read out and output from the ROM 34. These processes can be performed by the setting means 101.

(2) Intensity Variable in Stimulus Pattern Modulation Processing

Since this intensity variable process is, in principle, similar to the above-described frequency variable process, the frequency as illustrated in FIG. 12 is merely substituted by the intensity (amplitude) for the intensity variable process. However, to initialize the frequency, a control signal is sent from the setting means 101 to PTM 35 and thus, the frequency is automatically locked by this PTM 35. The stimulus pattern modulation is carried out by such an intensity variable system whereby the voltage and current stimulus signals can be alternately applied to a biological body.

In both types of the stimulus pattern modulation processes, the stimulus patterns are controlled by the program previously stored in CPU 32.

As has been described, the current and voltage stimulus signals are alternately changed in this type of the stimulus pattern modulation system. The time period required for this signal change is selected to be from several seconds to several minutes. It is however preferable to select approximately two seconds to one minute.

The reason why such alternating stimulus employing the voltage and current stimulus signals may be applied to a biological body is as follows. When, for instance, the current control is performed as a sine wave and an exponential function waveform, and also the voltage control is performed as a rectangular wave and a pin-shaped waveform, no stimulus is given to the biological body in the current control, even if the same current value as in the voltage control method is used. Although the biological body feels no stimulus, it receives electric changes in the current control method, so that this current stimulus method is effective for a biological body under anesthesia, children, or a person who does not like to receive the electric stimulus signal. However, if current stimulus, by itself, causes no feeling in a biological body, the proper stimulus by alternately changing the voltage and current stimulus may be felt by the body.

Operation Flow of Main Control of Present Apparatus

FIG. 13 shows one example of a main control flow of the apparatus according to the present invention.

First, a check is made on whether or not the signal sent from the input section 20 is received (S50). If the input signal is received, then the subsequent frequency processing operation is performed, after the data used for the above judgement and each of the data has been set. If such an input signal is not yet received, the subsequent frequency processing operation is similarly carried out.

Thereafter, a judgement is made on whether or not the frequency modulation is performed (S52). If its command is made, then the control advances to the next processing step after the frequency modulation processing has been carried out (S53). If no command is made, the control directly advances to the succeeding process.

Thereafter, a judgement is made on whether or not the amplitude modulation is performed (S54). If its command is made, the control advances to the succeeding step after the amplitude modulation processing has been accomplished (S55). If no command is made, the control directly advances to the subsequent step.

Subsequently, a judgement is made on whether or not the rhythmic modulation is done (S56). If the command is made, then the control advances to the next processing step after the rhythmic modulation has been executed (S57). If no, then the control advances directly to the subsequent processing step.

Therefore, a judgement is made on whether or not the pulse number modulation is done (S58). If its command is made, the control advances to the subsequent processing step after the frequency modulation process has been performed (S59). If there is no command, the control directly advances to the next processing step.

Then, a judgement is made on whether or not modulation processing is done (S60). If no modulation command is made, the control advances to the next processing step after no modulation processing has been performed (S61). Otherwise, the control advances directly to the succeeding process step.

Then, in addition, a predetermined process such as a stimulus pattern process is controlled.

It should be noted that these signal processings are repeated during a series to operations of the low frequency stimulus signal generating apparatus. The judgement processings for judging the sorts of various modulation system are performed in the modulation system setting means 106 in CPU 32. The judgement results are sent to the respective frequency forcibly converting means 103, cure intensity setting means 104, pulse number setting means (105), and stimulus parameter setting means 107. Then, the proper signal process is effected.

Processing Sound Volume Level Data in CPU

Figure 14:
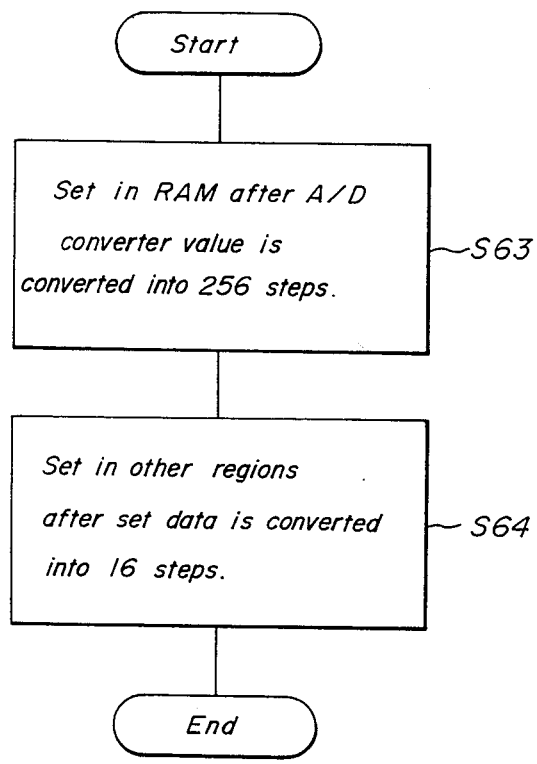

In FIG. 5, the sound volume level data which has been input from the A/D converter 92 into CPU 32, is converted into 8-bit data and set into RAM 33 by means of the converting means 102 as illustrated in the flowchart of FIG. 14 (S63). This data conversion is carried out in such a manner that the data value derived from the A/D converter 92 is converted into the 8-bit data having 256 steps. This set data is further converted into 16-stepped data and set into another field in RAM 33 (S64).

Current Stimulus Generating Circuit and Voltage Stimulus Generating Circuit

Then, a brief explanation will now be made of the current stimulus generating circuit 47 and voltage stimulus generating circuit 51, which has been described in FIG. 2, with reference to FIGS. 15 and 16.

It should be noted that both generating circuits 47 and 51 can be assembled by employing the conventional electronic circuit technology.

(1) Current Stimulus Signal Generating Circuit

In FIG. 15, there is shown a block diagram of the current stimulus signal generating circuit as one example. As previously described, this circuit is a circuit for outputting the current having the same waveform as that of the input voltage.

This generating circuit may be constructed of the first stage 110, second stage 120 and third stage 130, and arranged by, for instance, an operational amplifier, a photocoupler, a darlington circuit.

The first stage 110 is arranged by the operational amplifier 111 and the light emitting diode 112 of the photocoupler to convert the voltage waveform into the current waveform at a constant voltage level, and converts the input voltage into a photo-output.

The second stage 120 is arranged by the light receiving element 121 of the photocoupler, the current-to-voltage converting circuit 122 for converting the current supplied from the light receiving element into the voltage, and the operational amplifier 123 for amplifying the resultant voltage, so as to produce the voltage.

The third stage 130 produces output current by amplifying the voltage at the operational amplifier 131 and thereafter, by converting the amplified voltage into the current in the darlington circuit. In this case, the circuit arrangement is so designed in that even if the impedance of the biological body to which this output current is given is varied, the current having the same waveform as that of the voltage can be continuously output by feeding back the output of the darlington circuit 132 to the operational amplifier 131.

It should be noted that the circuit arrangement of this current stimulus signal generating circuit 46 is not limited to the above embodiment, but may be modified.

(2) Voltage Stimulus Generating Circuit

This circuit is a circuit for simply amplifying the input voltage, a circuit arrangement of which is shown in FIG. 16. This voltage stimulus generating circuit 51 is constructed of the operational amplifier 141 and push-pull amplifier 142 for amplifying the output from the operational amplifier, so as to output a voltage which is obtained by converting the amplitude and frequency of the input voltage into a predetermined voltage.

Similarly, this generating circuit 51 is not limited to the above-described circuit arrangement, but may be modified.

The control method and/or apparatus are not restricted to the above-described method and circuit arrangements to achieve the present invention, but may be modified within the technical scope and spirit of the invention.

For instance, the arrangement of the apparatus as illustrated in FIG. 2, may be constructed by employing other circuit arrangements. Similarly, the operation method may be modified.

It is also possible to generate the electric stimulus signal by combining more than two modulations selected from the above-described frequency modulation, amplitude modulation, pulse modulation, rhythmic modulation, and stimulus pattern modulation (alternate stimulus).

ADVANTAGES OF THE INVENTION

As has been described in detail, the low frequency electric stimulus in accordance with the sound volume (sound pressure) levels of the music and sounds can be provided to a biological body in substantially real time by alternately changing the current or voltage control system. As a result, the cure effects as well as the pain relaxation effects can be achieved according to the invention, as compared with the conventional cure system on the basis of the 1/f fluctuation theory.

According to the present invention, particularly, in a case of rhythm modulation, the current or voltage stimulus signal is controlled based upon the sound waveforms when the sound information is input. When no sound information is present, these voltage and current stimulus signals are controlled based upon the waveform of the quasi-sound waveform. Then, since one of these stimulus signals can be output as the electric stimulus signal in real time, the pain reduction and curing effects can be more improved as compared with the conventional 1/f fluctuation theory. In addition, since the present invention utilizes only the sound information containing the low frequencies lower than approximately 200 Hz such as bases and drums, the unpleasant feelings can be effectively eliminated by mainly obtaining the rhythmic feeling.

Furthermore, particularly, in a case of the inventions where the current stimulus signal and voltage stimulus signal are alternately switched-over to output as the electrical stimulus signal, since a biological body can be electrically stimulated in real time in accordance with the tempo of the favorable music, greater curing effects and pain reduction can be realized in the field of the musical curing method, as compared with the conventional musical curing method employing 1/f fluctuation theory. Furthermore, as the current and voltage control systems are alternately switched to provide such alternating stimulus to a biological body, it is possible to avoid no stimulus feeling for the biological body. Accordingly, the no feeling can be eliminated, the pain effect can be reduced and the curing effects can be improved. Moreover, since the low frequency electric stimulus signal is employed, relaxation can be expected both bodily and psychologically.

What is claimed is:

1. A method of providing electrical stimulus to a biological body, comprising the steps of:
   generating a low frequency electrical signal;
   frequency modulating either the current or voltage, or both, of the low frequency signal with frequencies corresponding to respective sound volume levels supplied by a sound source to stimulate the body.

2. The method of claim 1, wherein the frequency modulating step further comprises the steps of:
   sampling the respective sound volume levels at a predetermined level at which the body feels them in substantially real time; and
   converting the respective sound volume levels into frequencies within a low frequency region.

3. The method of claim 2, wherein the low frequency region has a frequency range of from 0 to 60 Hz.

4. The method of claim 2, wherein the sampling step comprises the step of:
   sampling within a time period from 0.01 to 0.5 second.

5. The method of claim 1, further comprising the steps of:
   converting the respective sound volume levels into pulse number control values; and
   pulse modulating the current or voltage of the signal.

6. A method of providing electrical stimulus to a biological body, comprising the steps of:
   generating a low frequency electrical signal;
   sampling respective sound levels at a predetermined rate at which the body feels them in substantially real time;
   converting the sampled respective sound levels into corresponding amplitude control values;
   amplitude modulating either the current or voltage, or both, of the low frequency signal to stimulate the body.

7. The method of claim 6, further comprising the steps of:
   converting the respective sound volume levels into pulse number control values; and
   pulse modulating the current or voltage of the signal.

8. The method of claim 7, further comprising the steps of:
   converting the respective sound volume levels into pulse number control values; and
   pulse modulating the current or voltage of the signal.

9. The method of claim 6, wherein the number of pulses for the pulse modulating step ranges from zero to thirty corresponding to the respective sound volume levels.

10. The method of claim 6, wherein the sampling step comprises the step of:
    sampling within a time period from 0.01 to 0.5 second.

11. A low frequency electric stimulus signal generating apparatus for applying electrical stimuli to a biological body, comprising: a stimulus signal generating section having:
    a control section for sampling respective sound volume levels derived from a sound source at a rate at which the body can substantially feel the sound volume levels in real time, the respective sampled sound levels being converted into corresponding low frequencies and output, and predetermined control information; and
    a current/voltage controlling section for independently frequency modulating current and voltage stimulus signals based upon the frequencies.

12. The apparatus of claim 11, wherein the stimulus signal generating section further comprises:
    a control system selecting section for switching either one of the current and voltage stimulus signals based upon control information derived from the control section, and for outputting the same as an electrical signal to stimulate the body.

13. The apparatus of claim 12, wherein the control section includes:
    a waveform generating section for generating a voltage waveform signal having frequencies corresponding to the respective sound volume levels; and
    a voltage stimulus signal generating circuit for outputting the voltage waveform signal as a voltage stimulus signal.

14. The apparatus of claim 11, wherein the current/voltage controlling section includes:
    a waveform generating section for outputting a voltage waveform signal having a waveform pattern corresponding to the sound volume levels; and
    a current stimulus signal generating circuit for outputting a current stimulus signal having the same waveform as that of an input voltage waveform signal.

15. The apparatus of claim 11, wherein the stimulus signal has a frequency region of between 0 to 60 Hz.

16. The apparatus of claim 11, wherein the control section samples the sound volume levels at a sampling period between 0.01 and 0.5 second.

17. The apparatus of claim 11, wherein the control section comprises:
    means for subdividing the sound volume levels into a plurality of level steps;
    memory means for storing a sound volume level to frequency conversion table; and
    means for reading out from the memory means frequencies corresponding to the respective sound volume levels for the sampling operation.

18. The apparatus of claim 17, wherein each of the sound volume levels is set to zero when it is equal to a predetermined zero, or a lower, level.

19. A method of generating a low frequency electrical stimulus signal to stimulate a biological body, comprising the steps of:
    deriving a waveform of sound information in response to a sound source;
    modulating at a rhythm at least the current or voltage of the electrical stimulus signal; and
    selecting a low frequency for the electrical stimulus signal.

20. The method of claim 19, wherein the deriving step further comprises the steps of:
    detecting presence of sound information;
    deriving only frequency information having a frequency lower than approximately 200 Hz from the detected sound information, the frequency information represented by waveforms;
    generating quasi-sound information having arbitrary waveforms when no sound information is detected; and
    utilizing the respective waveforms of the frequency information and the quasi-sound information to modulate the current and voltage of the electrical stimulus signal.

21. The method of claim 20, further comprising the step of:
   selectively adjusting the intensity of the electrical stimulus signal.

22. The method of claim 19, further comprising the step of:
   selectively adjusting the intensity of the electrical stimulus signal.

23. A low frequency electrical stimulus signal generating apparatus, comprises:
   an input section for setting and adjusting initial conditions to various inputting signals;
   a stimulus signal generating section including:
   a waveform control section for providing a rhythmic-modulated waveform signal derived from low frequency sound information from a sound source;
   a current control section for utilizing the rhythmic-modulated waveform signal to generate a current stimulus signal;
   a voltage control section for utilizing the rhythmic-modulated waveform signal to generate a voltage stimulus signal;
   a control system selecting section for providing at least one of the current stimulus signal and the voltage stimulus signal as an output electrical signal to stimulate a biological body; and
   a control section for controlling respective operations of the control section and the selecting section, based upon a signal derived from the input section.

24. The apparatus of claim 23, wherein the waveform control section comprises:
   a comparator for detecting the presence of sound information;
   a low pass filter for filtering low frequency sound information having a frequency lower than approximately 200 Hz;
   a rhythmic generator for generating quasi-sound information; and
   a selection switch for selecting the low frequency sound information when sound information is detected and the quasi-sound information when sound information is not detected.

25. The apparatus of claim 24, further comprising:
   intensity setting means for selectively adjusting the intensity of the electrical stimulus signal.

26. The apparatus of claim 23, wherein the current control section comprises:
   an intensity setting circuit for rhythmic-modulating the waveform signal; and
   a current stimulus signal generating circuit for outputting or current stimulus signal having the same waveform as that of a waveform input from the intensity setting circuit; and wherein the voltage control section comprises:
   a voltage stimulus circuit for adjusting the rhythmic-modulating waveform signal to provide an output voltage stimulus signal.

27. The apparatus of claim 26, further comprising:
   intensity setting means for selectively adjusting the intensity of the electrical stimulus signal.

28. The apparatus of claim 23, further comprising:
   intensity setting means for selectively adjusting the intensity of the electrical stimulus signal.

29. A low frequency electric stimulus signal generating apparatus comprising:
   a stimulus signal generating section including:
   a control section for sampling respective sound volume levels supplied from a sound source at a rate in which a biological body feels the volume levels in substantially real time, each of the sampled volume levels being converted into a corresponding amplitude control value and provided as an output, and for outputting predetermined control information; and
   a current/voltage control section for amplitude modulating current and voltage stimulus signals, in response to the amplitude control value, within a range of 0 to 100% of an initial set amplitude value.

30. The apparatus of claim 29, wherein the stimulus signal generating section further comprises:
   a control system selecting section for using the control information from the control section to select only one of the current and voltage stimulus signals as an output electric stimulus signal to stimulate the body.

31. The apparatus of claim 30, wherein the control section comprises:
   means for subdividing the sound volume levels into a plurality of level steps; and
   means for converting the subdivided levels into corresponding amplitude control values, and for outputting the converted control values.

32. The apparatus of claim 29, wherein the current/voltage control section comprises a current control section having:
   a waveform generating section for outputting a voltage waveform signal having an arbitrary frequency;
   an intensity setting circuit for using the amplitude control value to control the intensity of the voltage waveform signal; and
   a current stimulus signal generating circuit for outputting a current stimulus signal having the same waveform as that of the intensity controlled voltage waveform signal.

33. The apparatus of claim 32, wherein the frequency has a range of from 0 to 60 Hz.

34. The apparatus of claim 33, wherein the control section comprises:
   means for subdividing the sound volume levels into a plurality of level steps; and
   means for converting the subdivided levels into corresponding amplitude control values, and for outputting the converted control values.

35. The apparatus of claim 32, wherein the control section comprises:
   means for subdividing the sound volume levels into a plurality of level steps; and
   means for converting the subdivided levels into corresponding amplitude control values, and for outputting the converted control values.

36. The apparatus of claim 32, wherein the intensity setting circuit uses the amplitude control value having a range from 0 to 100% of the initial set amplitude value to obtain an electric stimulus signal having 24 level steps.

37. The apparatus of claim 29, wherein the current/voltage control section comprises a voltage control section having:
   a waveform generating section for outputting a voltage waveform signal having an arbitrary frequency; and
   a voltage stimulus signal generating circuit for using the amplitude control value to control the intensity of the voltage waveform signal and for outputting the intensity-controlled voltage waveform signal as a voltage stimulus signal.

38. The apparatus of claim 37, wherein the frequency has a range of from 0 to 60 Hz.

39. The apparatus of claim 38, wherein the control section comprises:
   means for subdividing the sound volume levels into a plurality of level steps; and
   means for converting the subdivided levels into corresponding amplitude control values, and for outputting the converted control values.

40. The apparatus of claim 37, wherein the control section comprises:
   means for subdividing the sound volume levels into a plurality of level steps; and
   means for converting the subdivided levels into corresponding amplitude control values, and for outputting the converted control values.

41. The apparatus of claim 29, wherein the control section samples the sound volume levels within time periods from 0.01 to 0.5 second.

42. The apparatus of claim 29, wherein the control section comprises:
   means for subdividing the sound volume levels into a plurality of level steps; and
   means for converting the subdivided levels into corresponding amplitude control values, and for outputting the converted control values.

43. A method of generating a low frequency electric stimulus signal, comprising the steps of:
   generating current and voltage stimulus signals to be provided to a biological body;
   reading out control information previously stored in a control section without using acoustic information from a sound source;
   utilizing the control information to control the current and voltage stimulus signals; and
   alternately outputting the current and voltage stimulus signals to stimulate the body.

44. The method of claim 43, further comprising the steps of:
   selecting the control information of the current and voltage stimulus signals from a plurality of waveforms, frequencies and intensities, the control information being selectable and variable externally.

45. The method of claim 44, further comprising the step of:
   randomly effecting the alternate outputting of the current and voltage stimulus signals.

46. The method of claim 45, wherein the randomly effecting step comprises the step of:
   randomly setting a time interval from several seconds to several tens of seconds to alternately output the current and voltage stimulus signals.

47. The method of claim 46, further comprising the step of:
   selecting a frequency of between 0 to 60 Hz for the electric stimulus signal.

48. The method of claim 45, further comprising the step of:
   selecting a frequency of between 0 to 60 Hz for the electric stimulus signal.

49. The method of claim 44, further comprising the step of:
   selecting a frequency of between 0 to 60 Hz for the electric stimulus signal.

50. The method of claim 43, further comprising the step of:
   randomly effecting the alternate outputting of the current and voltage stimulus signals.

51. The method of claim 50, wherein the randomly effecting step comprises the step of:
   randomly setting a time interval from several seconds to several tens of seconds to alternately output the current and voltage stimulus signals.

52. The method of claim 51, further comprising the step of:
   selecting a frequency of between 0 to 60 Hz for the electric stimulus signal.

53. The method of claim 50, further comprising the step of:
   selecting a frequency of between 0 to 60 Hz for the electric stimulus signal.

54. The method of claim 43, further comprising the step of:
   selecting a frequency of between 0 to 60 Hz for the electric stimulus signal.

55. A low frequency electric stimulus signal generating apparatus, comprising:
   an input section for setting and adjusting initial conditions to various inputting signals; and
   a stimulus signal generating section including:
   a control section for storing control information, the information being readily accessible;
   a current control section for using the control information to generate a current stimulus signal;
   a voltage control section for using the control information to generate a voltage stimulus signal; and
   a control system selection section for using the control information to alternately select the current stimulus signal and the voltage stimulus signal as an output electric stimulus signal to stimulate a biological body.

56. The apparatus of claim 55, wherein the control information for the current and voltage stimulus signals is selected from a plurality of waveforms, frequencies and intensities, the control information being selectable and variable externally.

57. The apparatus of claim 56, wherein the control system selection section alternately selects the current and voltage stimulus signals at random.

58. The apparatus of claim 57, wherein the control system selection section randomly sets a time interval from several seconds to several tens of seconds to alternately output the current and voltage signals.

59. The apparatus of claim 58, wherein the electric stimulus signal has a frequency between 0 to 60 Hz.

60. The apparatus of claim 57, wherein the electric stimulus signal has a frequency between 0 to 60 Hz.

61. The apparatus of claim 56, wherein the electric stimulus signal has a frequency between 0 to 60 Hz.

62. The apparatus of claim 55, wherein the control system selection section alternately selects the current and voltage stimulus signals at random.

63. The apparatus of claim 62, wherein the control system selection section randomly sets a time interval from several seconds to several tens of seconds to alternately output the current and voltage signals.

64. The apparatus of claim 63, wherein the electric stimulus signal has a frequency between 0 to 60 Hz.

65. The apparatus of claim 62, wherein the electric stimulus signal has a frequency between 0 to 60 Hz.

66. The apparatus of claim 55, wherein the electric stimulus signal has a frequency between 0 to 60 Hz.

* * * * *

UNITED STATES PATENT AND TRADEMARK OFFICE
CERTIFICATE OF CORRECTION

PATENT NO. : 4,875,484

DATED : October 24, 1989

INVENTOR(S) : Hiroshi Anzai, et al.

It is certified that error appears in the above-identified patent and that said Letters Patent is hereby corrected as shown below:

Column 1, line 11, change "electrical" to --electric--.

Column 1, line 12, change "electrical" to --electric--.

Column 3, line 32, change "concluded" to --included--.

Column 4, line 27, change "then" to --than--.

Column 4, line 68, change "embodiments" to --embodiment,--.

Column 5, line 44, change "irregular" to --irregularly--.

Column 5, bridging lines 57 and 58, change "embodiment" to
--embodiments--.

Column 6, line 36, change "seconds" to --second--.

Column 6, line 50, before "the" insert --modulate--.

Column 7, line 40, after "generating" insert --section--.

Column 7, line 68, delete "embodi-".

Column 8, line 1, delete "ments" and after "seventh" insert
--embodiments--.

UNITED STATES PATENT AND TRADEMARK OFFICE
CERTIFICATE OF CORRECTION

PATENT NO. : 4,875,484
DATED : October 24, 1989
INVENTOR(S) : Hiroshi Anzai, et al.

It is certified that error appears in the above-identified patent and that said Letters Patent is hereby corrected as shown below:

Column 8, line 3, after "irregularly" insert --modulate--.

Column 8, line 7, after "can" insert --receive--.

Column 8, line 16, change "embodiment" to --embodiments--.

Column 9, line 17, change "devices" to --device--.

Column 10, line 55, change "process" to --processes--.

Column 10, bridging lines 58 and 59, change "process" to --processes--.

Column 12, line 14, change "system" to --systems--.

Column 14, line 53, change "periods" to --period--.

Column 15, line 43, change "judgement" to --judgment--.

Column 15, line 46, change "judgement" to --judgment--.

Column 15, line 51, change "judgement" to --judgment--.

Column 15, line 56, delete "of this frequency" (second occurrence).

Column 16, line 49, change "is" to --are--.

Column 18, line 22, change "stron" to --strong--.

Column 18, line 31, change "judgement" to --judgment--.

UNITED STATES PATENT AND TRADEMARK OFFICE
CERTIFICATE OF CORRECTION

PATENT NO. : 4,875,484
DATED : October 24, 1989
INVENTOR(S) : Hiroshi Anzai, et al.

It is certified that error appears in the above-identified patent and that said Letters Patent is hereby corrected as shown below:

Column 18, line 63, after "Hz" insert --is--.

Column 20, line 29, change "judgement" to --judgment--.

Column 20, line 33, change "judgement" to --judgment--.

Column 20, line 39, change "judgement" to --judgment--.

Column 20, line 45, change "judgement" to --judgment--.

Column 20, line 51, change "judgement" to --judgment--.

Column 20, line 57, change "judgement" to --judgment--.

Column 20, line 68, change "judgement" to --judgment--.

Column 21, line 1, change "system" to --systems--.

Column 21, line 2, change "judgement" to --judgment--.

Signed and Sealed this

Twenty-fifth Day of February, 1992

Attest:

HARRY F. MANBECK, JR.

*Attesting Officer*         *Commissioner of Patents and Trademarks*